United States Patent
Valencia et al.

(10) Patent No.: US 11,912,769 B2
(45) Date of Patent: *Feb. 27, 2024

(54) METHODS OF TREATING SYSTEMIC LUPUS ERYTHEMATOSUS USING A DOMAIN ANTIBODY DIRECTED AGAINST CD28

(71) Applicant: BRISTOL-MYERS SQUIBB COMPANY, Princeton, NJ (US)

(72) Inventors: Xavier Valencia, Princeton, NJ (US); John P. Throup, New Hope, PA (US); Steven G. Nadler, Princeton, NJ (US); Suzanne J. Suchard, Portland, OR (US); Dominique Duchesne, Yardley, PA (US); Xiaoni Liu, Yardley, PA (US); Rong Shi, Princeton, NJ (US); Diane E. Shevell, Westfield, NJ (US); Jenny H. Xie, Princeton, NJ (US); Marek Honczarenko, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/584,207

(22) Filed: Jan. 25, 2022

(65) Prior Publication Data

US 2022/0144951 A1 May 12, 2022

Related U.S. Application Data

(63) Continuation of application No. 16/842,885, filed on Apr. 8, 2020, now Pat. No. 11,267,888, which is a continuation of application No. 15/515,461, filed as application No. PCT/US2015/053233 on Sep. 30, 2015, now abandoned.

(60) Provisional application No. 62/057,981, filed on Sep. 30, 2014.

(51) Int. Cl.
| | |
|---|---|
| *A61K 39/395* | (2006.01) |
| *C07K 16/28* | (2006.01) |
| *A61K 47/60* | (2017.01) |
| *A61K 45/06* | (2006.01) |
| *A61K 39/00* | (2006.01) |

(52) U.S. Cl.
CPC ...... *C07K 16/2818* (2013.01); *A61K 39/3955* (2013.01); *A61K 45/06* (2013.01); *A61K 47/60* (2017.08); *A61K 2039/505* (2013.01); *A61K 2039/54* (2013.01); *A61K 2039/545* (2013.01); *C07K 2317/24* (2013.01); *C07K 2317/565* (2013.01); *C07K 2317/569* (2013.01); *C07K 2317/76* (2013.01); *C07K 2317/92* (2013.01); *C07K 2317/94* (2013.01); *C07K 2319/31* (2013.01)

(58) Field of Classification Search
CPC .................................................. C07K 16/2818
See application file for complete search history.

(56) References Cited

U.S. PATENT DOCUMENTS

| | | | |
|---|---|---|---|
| 11,267,888 B2* | 3/2022 | Valencia | A61K 47/60 |
| 2010/0028354 A1* | 2/2010 | McKinnon | A61P 1/04 |
| | | | 424/139.1 |
| 2017/0240636 A1 | 8/2017 | Valencia et al. | |

FOREIGN PATENT DOCUMENTS

| | | |
|---|---|---|
| WO | WO2010009391 A1 | 1/2010 |
| WO | WO2014120916 A1 | 8/2014 |
| WO | WO2015143209 A1 | 9/2015 |
| WO | WO2016054218 A1 | 4/2016 |

OTHER PUBLICATIONS

Muller, P. et al. "The minimum anticipated biological effect level (MABEL) for selection of first human dose in clinical trials with monoclonal antibodies," Current Opinion in Biotechnology, London, GB, vol. 20, No. 6, pp. 722-729, 2009.
S.J. Suchard et al., "A Monovalent Anti-Human CD28 Domain Antibody Antagonist: Preclinical Efficacy and Safety", The Journal of Immunology, vol. 191, No. 9, Nov. 1, 2013, pp. 4599-4610.
International Preliminary Report on Patentability dated Apr. 4, 2017.

* cited by examiner

*Primary Examiner* — Albert M Navarro

(57) ABSTRACT

Methods of treating autoimmune diseases, such as systemic lupus erythematosus using domain antibodies that specifically bind human CD28 are provided. The methods may comprise at least one administration cycle comprising one dose of the domain antibody. The method reduces symptoms of systemic lupus erythematosus compared to placebo.

15 Claims, 4 Drawing Sheets

Specification includes a Sequence Listing.

METHODS OF TREATING SYSTEMIC LUPUS ERYTHEMATOSUS USING A DOMAIN ANTIBODY DIRECTED AGAINST CD28

CROSS-REFERENCE TO RELATED APPLICATION

This application is a continuation application of U.S. patent application Ser. No. 16/842,885 filed Apr. 8, 2020, which is a continuation application of U.S. patent application Ser. No. 15/515,461 filed Mar. 29, 2017, which is a 35 U.S.C. § 371 National Stage Patent application of International Application PCT/US2015/053233, filed Sep. 30, 2015 which claims priority to U.S. Provisional Applications Serial application Ser. No. 62/057,981, filed Sep. 30, 2014, the entire contents of which are incorporated herein by reference.

FIELD OF THE INVENTION

Methods of treating autoimmune diseases, such as systemic lupus erythematosus using domain antibodies that specifically bind human CD28 are provided

SEQUENCE LISTING

Reference to a Sequence Listing is submitted electronically herewith and is incorporated herein by reference.

BACKGROUND

Systemic lupus erythematosus (SLE) is a chronic progressive autoimmune disease characterized by pleiotropic organ/tissue involvement and clinical manifestations. The progression of the disease is punctuated by flares, which by definition require therapy modification. Uncontrolled SLE will lead to end organ damage with increased morbidity and mortality. The clinical manifestations are variegated and often in a single patient many organs and tissue are involved. Most commonly targeted tissues are skin (with the typical malar or butterfly rush), joints and kidney, but practically any organ and tissue can be targeted.

Autoantibodies, such as anti-double-stranded deoxyribonucleic acid (anti-dsDNA) or anti-nuclear antibody (ANA), have helped to define the autoimmune nature of SLE. These autoantibodies, however, are not pathognomonic. SLE, with its pleiotropic clinical manifestations and lack of specific autoantibodies is the archetype of the non-organ specific autoimmune diseases. American College of Rheumatology (ACR) has developed an 11 factor set of guidelines to diagnose SLE. This intrinsic complexity for diagnosis and monitoring disease progression has hampered the validation of new treatments.

The full pathogenic cascade leading to SLE, with all its clinical facets, is complex and not yet fully defined. Despite this, it is now well accepted that T cells have a pivotal role in SLE. SLE is characterized by hyper-responsive T cells, excessive autoantibody production, and antigen presenting cell (APC) hyperactivation. The autoantibodies (in particular, anti-nuclear antibodies, and anti-dsDNA antibodies) in SLE patients are dependent on T-cell help that is provided by co-stimulatory molecules and cytokines. In addition to providing B-cell help, T cells can directly infiltrate the joints, skin, kidney, and brain causing damage directly through cytotoxicity or indirectly through the recruitment and activation of macrophages and neutrophils.

Lymphocytes from patients with SLE show signs of increased activation; e.g., the percentage of CD4+ T cells expressing CD25 increase as does the expression of CD86 on CD19+ B cells. The increased CD86 expression is thought to render (autoreactive) B cells more susceptible to T-cell help and thus facilitate autoantibody production. Consistent with this observation, the number of activated B cells and levels of anti-dsDNA antibodies increase with diseased activity. In addition, peripheral blood dendritic cells (DCs) and DCs derived from peripheral blood monocytes of SLE patients show increased expression of CD86 and the ratio of CD86/CD80 is higher in SLE patients compared with healthy donors. Unlike CD86, CD28 expression on CD4+ and CD8+ T cells in lupus patients appears to be more variable. Regardless of the levels of CD28 expression, T cells from SLE patients appear to be more responsive to anti-CD28-mediated activation and patients with active disease have increased gene expression of CD28 when compared to normal controls. CTLA4 (a co-inhibitory molecule) is also increased in T cells from SLE patients but this does not seem to control aberrant T-cell activation. Taken together, these data suggest that the CD28-CD86/CD80 pathway plays a central role in the defective immune response observed in SLE patients.

Currently SLE patients are treated, depending on the severity of the disease, with antimalarials, corticosteroids (CS), such as oral prednisone and immunosuppressive drugs such as MTX, AZA, mycophenolate mofetil, and cyclophosphamide. Although corticosteroids and immunosuppressive drugs are generally effective in temporarily controlling flares and disease progression, their reduced efficacy and serious adverse effects significantly limit their prolonged use. This has led to the off-label use of many medicines to treat Lupus patients. The paucity of satisfactory therapeutic options is stressed by the approval of only one new medicine (Belimumab) for SLE in the last fifty years. Despite Belimumab approval SLE patients still have a very high unmet medical need and novel therapies are needed to satisfactorily treat SLE.

Inhibition of CD28 mediated T cell activation could inhibit undesired T cell responses occurring during autoimmunity, transplant rejection, or allergic responses. For example, inhibiting CD28 mediated T cell activation could delay graft rejection, prevent acute allograft rejection, induce donor specific tolerance, and prevent development and interrupt the progression of chronic allograft rejection, as well as prevent graft versus host disease (GVH), i.e., when transplanted T cells mount a vigorous immune response against host tissue alloantigens (Salama et al. (2001) *J. Clin. Invest.* 108: 943-48). Not only would inhibiting CD28 mediated T cell activation dampen the immune response through negating activation signaling through CD28, it should not impact the interaction of CD86 and CD80 to CTLA4, thereby preserving CTLA4 mediated inhibition of the T cell response. Thus, inhibiting CD28 mediated T cell activation could be used to prevent induction of autoimmunity and moderate the progression and/or severity of lupus as well as other autoimmune diseases. (Saloman et al. (2001) *Ann. Rev. Immunol.* 19: 225-252).

Accordingly, it is an object of this invention to provide improved methods for treating subjects with SLE without stimulation of CD28 signaling pathways.

SUMMARY

In certain embodiments, the present invention provides a method of treating an immune disease in a patient, comprising administering to the patient a therapeutically effective amount of an anti-CD28 domain antibody which comprises a variable domain, wherein the variable domain comprises the amino acid sequence of SEQ ID NO: 12 (1h-239-891(D70C)) or differs from SEQ ID NO: 12 by up to 5 amino acids, wherein at least one dose of the anti-CD28 domain antibody is administered at a dose from about 1.25 mg to about 12.5 mg. In a specific embodiments, the immune disease is systemic lupus erythematosus (SLE). Preferably, the patient is a human patient.

In certain aspects, the anti-CD28 domain antibody is administered at a dose selected from about 1.25 mg, about 5 mg, and about 12.5 mg. For example, the dose is at least 1.25 mg or at least 5 mg. Optionally, the dose is about 1.25 mg, about 5 mg, or about 12.5 mg. Optionally, the dose is administered every week or every two weeks. Optionally, at least 2 doses are administered, wherein the at least 2 doses are the same or different. For example, at least 12 doses are administered. For example, at least 24 doses are administered.

In certain aspects, the variable domain of the anti-CD28 domain antibody comprises: (1) a CDR1 region having the amino acid sequence of SEQ ID NO: 1; (2) a CDR2 region having the amino acid sequence of SEQ ID NO: 2; and (3) a CDR3 region having the amino acid sequence of SEQ ID NO: 3. To illustrate, the anti-CD28 domain antibody comprises the amino acid sequence of SEQ ID NO: 12. Optionally, the anti-CD28 domain antibody comprises a 40 kDa branched polyethylene glycol. In certain specific embodiments, the anti-CD28 domain antibody is BMS-931699.

In certain aspects, the anti-CD28 domain antibody is administered subcutaneously. For example, the anti-CD28 domain antibody is formulated in a pharmaceutical composition for subcutaneous administration. Alternatively, the anti-CD28 domain antibody is administered intravenously. For example, the anti-CD28 domain antibody is formulated in a pharmaceutical composition for intravenous administration.

In certain aspects, the method of the invention further comprises administering to the patient an immunosuppressive/immunomodulatory and/or anti-inflammatory agent. Optionally, the immunosuppressive/immunomodulatory and/or anti-inflammatory agent is administered before the anti-CD28 domain antibody. Optionally, the immunosuppressive/immunomodulatory and/or anti-inflammatory agent is administered after the anti-CD28 domain antibody. Optionally, the immunosuppressive/immunomodulatory and/or anti-inflammatory agent is administered concurrently with the anti-CD28 domain antibody.

Included is method of antagonizing CD28, comprising administering an effective amount of an anti-CD28 domain antibody (dAb) disclosed herein to an individual. Also included is a method of antagonizing the binding of CD28 comprising administering an effective amount of the anti-CD28 dAb disclosed herein to an individual, wherein the anti-CD28 dAb antagonizes the binding of CD28 to CD80 and/or CD86 in the individual.

Further included is a method of treating, alleviating, or preventing a symptom of an immune disease, such as an autoimmune disease or a graft-related disease, comprising administering an effective amount of an anti-CD28 dAb disclosed herein to an individual having or at risk of having an immune disease. Included is a method of treating, alleviating, or preventing an immune disease, comprising administering an effective amount of an anti-CD28 dAb disclosed herein to an individual having or at risk of having an immune disease.

Included is the use of an anti-CD28 dAb disclosed herein for preparing a medicament for treating or preventing an immune disease in a patient in need thereof. Also included is the use of an anti-CD28 dAb disclosed herein for preparing a medicament for treating or preventing a symptom of an immune disease in a patient in need thereof. Further included herein is the use of an anti-CD28 dAb disclosed herein for preparing a medicament for alleviating at least one symptom of an immune disease in a patient in need thereof.

Further provided is an anti-CD28 domain antibody formulated in a pharmaceutical composition for subcutaneous administration. The pharmaceutical composition may further comprise a pharmaceutically acceptable carrier. The domain antibody may be administered subcutaneously.

A kit for treating an immune disease in a patient is also provided, the kit comprising: (a) a dose of domain antibody comprising an anti-CD28 domain antibody, and (b) instructions for using the domain antibody in the disclosed methods.

DETAILED DESCRIPTION

Figure 1:
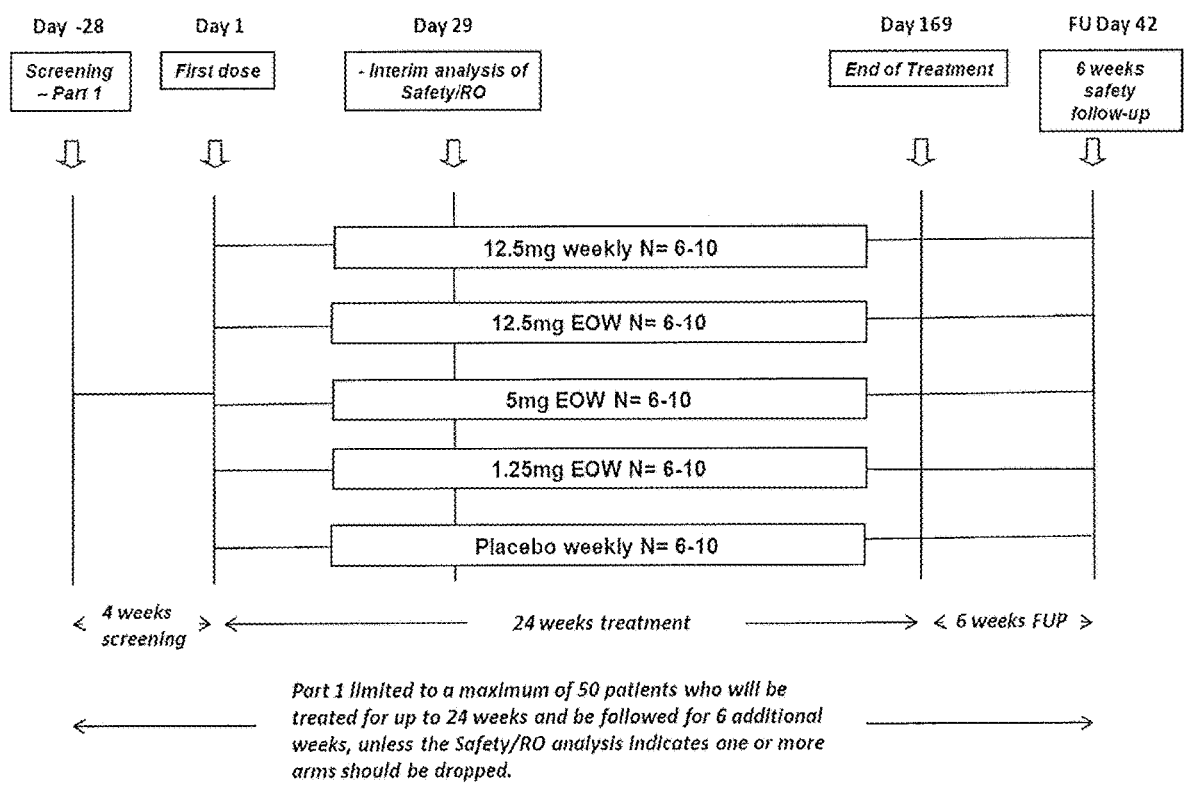
FIG. 1 shows Part 1 of an FDA Phase 2 parallel-arm, randomized, double-blinded, multicenter, international study, adaptive design schematic for BMS-931699.

The present disclosure provides anti-CD28 domain antibodies to antagonize CD28 activity and methods of treating immune diseases, such as lupus, using said domain antibodies. The domain antibodies may be linked to polymers to improve pharmacokinetic properties, such as stability and half-life. Included herein are compositions and methods for the attachment of polymer molecules (e.g., polyethylene glycol; PEG) to proteins to modulate the pharmacokinetic properties of the modified proteins. For example, PEG modification of proteins has been shown to alter the in vivo circulating half-life, antigenicity, solubility, and resistance to proteolysis of the protein (Abuchowski et al. (1977) *J. Biol. Chem.*, 252: 3578; Nucci et al. (1991) *Adv. Drug Delivery Reviews* 6: 133; Francis et al., *Pharmaceutical Biotechnology* Vol. 3 (Borchardt, R. T. ed.); and Stability of Protein Pharmaceuticals: in vivo Pathways of Degradation and Strategies for Protein Stabilization 1991 pp 235-263, Plenum, NY).

The disclosed domain antibodies, including BMS-931699 (otherwise known as lulizumab or 1h-239-891(D70C) formatted with a 40 kDa branched polyethylene glycol), monovalently bind CD28, and inhibit the interaction of CD80 and CD86 with CD28, the key co-stimulatory receptor of T lymphocytes. Ultimately, targeting CD28 with the domain antibodies can provide opportunity to inhibit autoimmune processes leading to systemic lupus erythematosus among other graft-related or autoimmune diseases. Such monovalent domain antibodies can also avoid potential undesirable effects that can occur with antibodies capable of divalent or multivalent binding of CD28. Domain antibodies described herein also do not block the interaction of CD80 and CD86 to CTLA4. The domain antibodies described herein do not cross-react with CTLA4, and thus do not bind the common motif on CTLA4 and CD28 that binds CD80/86. The domain antibodies can thus provide improved therapeutic benefits and reduced side-effects for autoimmune disease patients. The domain antibody thus offers a novel therapeutic modality, currently not available to patients. Given the lack of therapeutic options for systemic lupus erythematosus and autoimmune disease subjects who have failed all conventional therapies, the domain antibody with its distinct mechanism of action and known safety profile demonstrates a favorable Risk/Benefit profile.

1. Definitions

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. Unless otherwise stated, all ranges described herein are inclusive of the specific endpoints. The following terms are provided below.

As used herein, a "fixed dose" is a dose administered regardless of the subjects' body weight.

As used herein, the term "human" when applied to a domain antibody or to an immunoglobulin variable domain means that the polypeptide has a sequence derived from a human immunoglobulin. A sequence is "derived from" a human immunoglobulin coding sequence when the sequence is either: a) isolated from a human individual or from cells or a cell line from a human individual; b) isolated from a library of cloned human antibody gene sequences (or a library of human antibody V domain sequences); or c) when a cloned human antibody gene sequence (or a cloned human V region sequence (including, e.g., a germline V gene segment)) was used to generate one or more diversified sequences that were then selected for binding to a desired target antigen.

At a minimum, a human domain antibody has at least 70% identical, at least 75% identical, at least 80% identical, at least 85% amino acid identity (including, for example, 87%, 90%, 93%, 95%, 97%, 99%, or higher identity) to a naturally-occurring human immunoglobulin variable domain sequence, e.g., a naturally-occurring human immunoglobulin variable domain sequence disclosed in Kabat ("Sequences of Proteins of Immunological Interest", US Department of Health and Human Services 1991).

As used herein, the term "domain" refers to a folded protein structure which retains its tertiary structure independently of the rest of the protein. Generally, domains are responsible for discrete functional properties of proteins, and in many cases may be added, removed, or transferred to other proteins without loss of function of the remainder of the protein and/or of the domain.

By "domain antibody" is meant a folded polypeptide domain which comprises a sequence characteristic of immunoglobulin variable domains and which specifically binds an antigen (e.g., dissociation constant of 500 nM or less). A "domain antibody" therefore includes complete antibody variable domains as well as modified variable domains, for example in which one or more loops have been replaced by sequences which are not characteristic of antibody variable domains, or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Where necessary or in case of any doubt, the numbering convention and boundaries set forth by Kabat et al. (Kabat et al. (1991) *Sequences of Immunological Interest*, 5$^{th}$ ed. U.S. Dept. Health & Human Services, Washington, D.C.) are applicable to immunoglobulin variable and constant domains referred to herein.

A "dAb" is used interchangeably with "domain antibody" herein. A "domain antibody" or "dAb" used in the present invention refers to an "anti-CD28 domain antibody".

As used herein, the phrase "sequence characteristic of immunoglobulin variable domains" refers to an amino acid sequence that is identical, over 20 or more, 25 or more, 30 or more, 35 or more, 40 or more, 45 or more, or even 50 or more contiguous amino acids, to a sequence comprised by an immunoglobulin variable domain sequence. Sequences similar or identical (e.g., at least about 70% sequence identity) to the sequences disclosed herein are also included herein.

As used herein, the term "identity" refer to the degree with which two nucleotide or amino acid sequences structurally resemble each other. As used herein, sequence "similarity" is a measure of the degree to which amino acid sequences share similar amino acid residues at corresponding positions in an alignment of the sequences. Amino acids are similar to each other where their side chains are similar. Specifically, "similarity" encompasses amino acids that are conservative substitutes for each other. A "conservative" substitution is any substitution that has a positive score in the blosum62 substitution matrix (Hentikoff and Hentikoff (1992) *Proc. Natl. Acad. Sci. USA* 89: 10915-10919). By the statement "sequence A is n % similar to sequence B" is meant that n % of the positions of an optimal global alignment between sequences A and B consists of identical amino acids or conservative substitutions. Typical conservative substitutions are exchanges among Met, Val, Leu, and Ile; among Ser and Thr; among the residues Asp, Glu, and Asn; among the residues Gln, Lys, and Arg; or aromatic residues Phe and Tyr.

As used herein, the term "epitope" refers to a unit of structure conventionally bound by an immunoglobulin $V_H/V_L$ pair. Epitopes define the minimum binding site for an antibody, and thus represent the target of specificity of an antibody. In the case of a domain antibody, an epitope represents the unit of structure bound by a domain antibody in isolation. That is, the binding site is provided by one, single immunoglobulin variable domain. Epitopes can be linear or conformational, and can be as small as three amino acids.

As used herein, "CD28 activity" is an activity involving or resulting from the binding of CD80, CD86 and/or another ligand to CD28, and includes, but is not limited to, activation of CD28-mediated cell signaling. CD28 activity also includes the induction of T cell proliferation and the induction of cytokine secretion, e.g., interleukin 2 (IL-2), by T cells.

As used herein, the term "does not substantially agonize" means that a given agent, e.g., a domain antibody, does not substantially activate one or more of the CD28 activities as the term "activate" is defined herein. Specifically, an agent that "does not substantially agonize" means that the agent does not activate more than 20% of the activity which is activated by CD80 and/or CD86 binding to CD28, and in an aspect, the agent does not activate more than about 10%, 8%, 5%, 3%, or 2% or less, including zero activation, of the activity which is activated by CD80 and/or CD86 binding to CD28. By way of a non-limiting example, a domain antibody set forth herein that does not substantially agonize CD28 activity does not agonize CD28 activity more than 5% of the activity obtained upon agonism of CD28 activity by anti-CD28 mAb 9.3 (Gibson, et al. (1996) *JBC*, 271: 7079-7083) under otherwise identical assay conditions.

As used herein, the terms "inhibit," "inhibits" and "inhibited" refer to a decrease in a given measurable activity (e.g., binding activity) by at least 10% relative to a reference. Where inhibition is desired, such inhibition is at least about 20%, 30%, 40%, 50%, 60%, 70%, 80%, 90%, or more, up to and including 100%, i.e., complete inhibition or absence of the given activity. Inhibition of CD28 binding to CD80 or CD86 can be measured as described in the working examples herein. As used herein, the term "substantially inhibits" refers to a decrease in a given measurable activity (e.g., the binding of CD28 to CD80 or CD86) by at least 50% relative to a reference. For example, "substantially inhibits" refers to a decrease in a given measurable activity of at least about 50%, 55%, 60%, 65%, 70%, 75%, 80%, 85%, 90%, 95%, and up to and including 100% relative to a reference. As used herein, "inhibits the binding", with reference to the binding of a domain antibody binding to CD28, or CD80 binding to CD28, or CD86 binding to CD28, refers to a decrease in binding by at least 10% relative to a reference. "Inhibits the binding" refers to a decrease in binding of at least about 20%, 30%, 40%, 50%, 60%, 70%, 80%, 90%, or more, up to and including 100%.

As used herein, the terms "activate," "activates" and "activated" refer to an increase in a given measurable activity by at least 5% relative to a reference, for example, at least 10%, 25%, 50%, 75%, or even 100%, or more.

As used herein, the term "monovalent" means that a given domain antibody can bind only a single molecule of its target. Naturally-occurring antibodies are generally divalent, in that they have two functional antigen-binding loops, each comprising a VH and a VL domain. Where steric hindrance is not an issue, a divalent antibody can bind two separate molecules of the same antigen. In contrast, a "monovalent" antibody has the capacity to bind only one such antigen molecule. As the term is used herein, a "monovalent" antibody can also comprise more than one antigen binding site, e.g., two antigen binding sites, but the binding sites must be for different antigens, such that the antibody can only bind one molecule of CD28 at a time. The antigen-binding domain of a monovalent antibody can comprise a $V_H$ and a $V_L$ domain, but in an aspect, comprises only a single immunoglobulin variable domain, i.e., a $V_H$ or a $V_L$ domain, that has the capacity to bind CD28 without the need for a corresponding $V_L$ or $V_H$ domain, respectively. A monovalent antibody lacks the capacity to cross link molecules of a single antigen.

As used herein, the terms "$V_H$ domain" and "$V_L$ domain" refer to immunoglobulin variable regions as defined by Kabat et al. (Kabat et al. (1991) *Sequences of Immunological Interest*, 5$^{th}$ ed. U.S. Dept. Health & Human Services, Washington, D.C.), which is incorporated herein by reference.

As used herein, "linked" refers to the attachment of a polymer moiety, such as PEG to an amino acid residue of a domain antibody. Attachment of a PEG polymer to an amino acid residue of a domain antibody, e.g., a domain antibody, is referred to as "PEGylation" and may be achieved using several PEG attachment moieties including, but not limited to N-hydroxylsuccinimide (NHS) active ester, succinimidyl propionate (SPA), maleimide (MAL), vinyl sulfone (VS), or thiol. A PEG polymer, or other polymer, can be linked to a domain antibody at either a predetermined position, or may be randomly linked to the domain antibody molecule. The PEG polymer may be linked to a domain antibody at a predetermined position. A PEG polymer may be linked to any residue in a domain antibody, however, it is preferable that the polymer is linked to either a lysine or cysteine, which is either naturally occurring in the domain antibody or which has been engineered into the domain antibody, for example, by mutagenesis of a naturally occurring residue in the domain antibody to either a cysteine or lysine. PEG-linkage can also be mediated through a peptide linker attached to a domain antibody. That is, the PEG moiety can be attached to a peptide linker fused to a domain antibody, where the linker provides the site, e.g., a free cysteine or lysine, for PEG attachment. As used herein, "linked" can also refer to the association of two or more domain antibodies, e.g., dAb monomers, to form a dimer, trimer, tetramer, or other multimer. Domain antibody monomers can be linked to form a multimer by several methods known in the art, including, but not limited to, expression of the domain antibody monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). While dAb multimers are specifically contemplated herein, e.g., in the context of dual- or multi-specific domain antibody constructs, it is emphasized that for any given domain antibody construct, the construct should only be able to bind one molecule of CD28, i.e., the constructs should have only one CD28-binding element, and should not cross link CD28.

As used herein, "polymer" refers to a macromolecule made up of repeating monomeric units, and can refer to a synthetic or naturally occurring polymer such as an optionally substituted straight or branched chain polyalkylene, polyalkenylene, or polyoxyalkylene polymer or a branched or unbranched polysaccharide. A "polymer" as used herein, specifically refers to an optionally substituted or branched chain poly(ethylene glycol), poly(propylene glycol), or poly (vinyl alcohol) and derivatives thereof.

As used herein, "PEG" or "PEG polymer" refers to polyethylene glycol, and more specifically can refer to a derivatized form of PEG, including, but not limited to N-hydroxylsuccinimide (NHS) active esters of PEG such as succinimidyl propionate, benzotriazole active esters, PEG derivatized with maleimide, vinyl sulfones, or thiol groups. For example, PEG formulations can include PEGO-CH$_2$CH$_2$CH$_2$—CO$_2$—NHS; PEG-O—CH$_2$—NHS; PEG-O—CH$_2$CH$_2$—CO$_2$—NHS; PEG-S—CH$_2$CH$_2$—CO—NHS; PEG-O$_2$CNH—CH(R)—CO$_2$—NHS; PEG-NHCO—CH$_2$CH$_2$—CO—NHS; and PEG-O—CH$_2$—CO$_2$—NHS; where R is (CH$_2$)$_4$)NHCO$_2$(mPEG). PEG polymers set forth herein may be linear molecules, or may be branched wherein multiple PEG moieties are present in a single polymer.

The attachment of PEG or another agent, e.g., HSA, to a domain antibody as described herein in an exemplary embodiment, will not impair the ability of the polypeptide to specifically bind CD28. That is, the PEG-linked domain antibody will retain its binding activity relative to a non-PEG-linked counterpart. As used herein, "retains activity" refers to a level of activity of a PEG-linked domain antibody which is at least 10% of the level of activity of a non-PEG-linked domain antibody, including at least about 20%, 30%, 40%, 50%, 60%, 70%, 80%, and up to 90%, including up to about 95%, 98%, and up to 100% of the activity of a non-PEG-linked domain antibody comprising the same antigen-binding domain or domains. More specifically, the activity of a PEG-linked domain antibody compared to a non-PEG linked domain antibody should be determined on a molar basis; that is equivalent numbers of moles of each of the PEG-linked and non-PEG-linked domain antibody should be used in each trial. In determining whether a particular PEG-linked domain antibody "retains activity", the activity of a PEG-linked domain antibody may be compared with the activity of the same domain antibody in the absence of PEG.

As used herein, the term "$IC_{50}$" refers to the concentration of an inhibitor necessary to inhibit a given activity by about 50%. $IC_{50}$ is determined by assaying a given activity, e.g., binding of CD28 to CD80 or CD86, in the presence of varying amounts of the inhibitor (e.g., domain antibody), and plotting the inhibitor concentration versus the activity being targeted. Binding of CD28 to CD80 or CD86 is measured herein by the method described the working examples. Alternatively, surface plasmon resonance (SPR) can be used.

As used herein, the term "$EC_{50}$" refers to the concentration of compound or domain antibody that provokes a response in a subject, wherein the response is halfway between the baseline and the maximum response. The baseline and maximum responses of a subject, with respect to a compound or domain antibody, can be determined by any technique known in the art.

As used herein, the term "fused to a domain antibody" generally means that a polypeptide is fused to a given antibody through use of recombinant DNA techniques, though fusion may occur chemically at the protein level. Thus, an antibody "fused to" another polypeptide, e.g., to another antibody of different binding specificity, does not exist in nature and is generated through recombinant means. The term "fused to a domain antibody" also encompasses the linkage of a polypeptide to a given domain antibody through, for example, disulfide or other chemical linkages, where the fused polypeptide is not naturally found fused to the domain antibody. Recombinant and chemical methods of fusing a polypeptide to another polypeptide, e.g., to an antibody, are well known in the art.

As used herein, the term "Fc domain" refers to the constant region antibody sequences comprising CH2 and CH3 constant domains as delimited according to Kabat et al., supra. The Fc portion of the heavy chain polypeptide has the ability to self-associate, a function which facilitates the formation of divalent antibodies. The term "lacks an Fc domain" means that a given domain antibody lacks at least the portion of an immunoglobulin Fc domain (as such domains are defined according to Kabat et al., 1991, *Sequences of Immunological Interest*, 5th ed. U.S. Dept. Health & Human Services, Washington, D.C.) sufficient to mediate the dimerization of Fc-containing domain antibodies. Dimerization of Fc-containing domain antibodies is measured, for example, by chromatographic methods or by surface plasmon resonance. A domain antibody lacking an Fc domain avoids Fc-platelet interactions and therefore avoids induction of platelet aggregation.

As used herein, the term "universal framework" refers to a single antibody framework sequence corresponding to the regions of an antibody conserved in sequence as defined by Kabat (Kabat et al. (1991) *Sequences of Immunological Interest*, 5th ed. U.S. Dept. Health & Human Services, Washington, D.C.) or corresponding to the human germline immunoglobulin repertoire or structure as defined by Chothia and Lesk, (1987) J. Mol. Biol. 196: 910-917. The use of a single framework, or a set of such frameworks, which has been found to permit the derivation of virtually any binding specificity though variation in the hypervariable regions alone, is included herein.

The term "about" will be understood by persons of ordinary skill in the art and will vary to some extent on the context in which it is used. Generally, about encompasses a range of values that are plus/minus 10% of a referenced value.

2. Anti-CD28 Domain Antibodies

The present invention relates to domain antibodies that specifically bind and inhibit human CD28 ("anti-CD28 domain antibodies") and that are useful in the treatment of diseases involving the CD28 pathway. Accordingly, a method of treating an immune disease in a patient in need of such treatment is provided comprising administering to the patient a therapeutically effective amount of the anti-CD28 domain antibody.

Domain antibodies are provided that are monovalent for binding to CD28. While not wishing to be bound by any particular theory, it is believed that monovalency for CD28 binding removes the possibility for cross-linking cell surface receptors that occurs with prior art antibodies. Thus, in one aspect, the domain antibodies disclosed herein not only inhibit or antagonize the binding of CD80 or CD86 to CD28, they do not substantially agonize CD28 activity.

In one aspect, the antibodies monovalent for CD28 binding are human domain antibodies. Human domain antibodies can be administered to human patients while largely avoiding the anti-antibody immune response often provoked by the administration of antibodies from other species, e.g., mouse. While murine antibodies can be "humanized" by grafting human constant domains onto the murine antigen-binding domains, human antibodies as disclosed herein are produced without the need for laborious and time-consuming genetic manipulation of a murine antibody sequence.

In certain embodiments, domain antibodies may include one or more of the following CDRs:

```
CDR1:
                                       (SEQ ID NO: 1)
RASRPIWPFLE

CDR2:
                                       (SEQ ID NO: 2)
FTSRLRH

CDR3:
                                       (SEQ ID NO: 3)
LQNVANPAT
```

In one embodiment, the anti-CD28 domain antibody has a CDR1 sequence that is at least 70%, 75%, 80%, 85%, 90%, 95%, 96%, 97%, 98%, or 99% identical to SEQ ID NO: 1.

In another embodiment, the CDR1 differs from SEQ ID NO: 1 by up to 5 amino acids (e.g., by 5, 4, 3, 2, 1, or 0 amino acids).

In one embodiment, the anti-CD28 domain antibody has a CDR2 sequence that is at least 70%, 75%, 80%, 85%, 90%, 95%, 96%, 97%, 98%, or 99% identical to SEQ ID NO: 2. In another embodiment, the CDR2 differs from SEQ ID NO: 2 by up to 5 amino acids (e.g., by 5, 4, 3, 2, 1, or 0 amino acids).

In one embodiment, the anti-CD28 domain antibody has a CDR3 sequence that is at least 70%, 75%, 80%, 85%, 90%, 95%, 96%, 97%, 98%, or 99% identical to SEQ ID NO: 3. In another embodiment, the CDR3 differs from SEQ ID NO: 3 by up to 5 amino acids (e.g., by 5, 4, 3, 2, 1, or 0 amino acids).

In certain embodiments, the anti-CD28 domain antibody comprises an amino acid sequence at least 70%, 75%, 80%, 85%, 90%, 95%, 96%, 97%, 98%, or 99% identical to an amino acid sequence selected from SEQ ID NOs: 4-15. In another embodiment, the anti-CD28 domain antibody differs from the selected amino acid sequence by up to 5 amino acids. For example, the domain antibody differs from SEQ ID NO: 12 by up to 5 amino acids (e.g., by 5, 4, 3, 2, 1, or 0 amino acids).

In certain embodiments, the anti-CD28 domain antibody comprises an amino acid sequence selected from SEQ ID NOs: 4-15. In a specific embodiment, the anti-CD28 domain antibody comprises the amino acid sequence of SEQ ID NO: 12.

Certain exemplary sequences of the anti-CD28 domain antibodies are provided below.

```
1h-239-891 (SEQ ID NO: 4):
DIQMTQSPSSLSASVGDRVTITCRASRPIWPFLEWYQQKPGKAPKLLIYFTSRLRHGVP
SRFSGSGSGTDFTLTISSLQPEDFATYYCLQNVANPATFSQGTKVEIKR 1h-239-891(Q3C) (SEQ ID NO: 5):
DICMTQSPSSLSASVGDRVTITCRASRPIWPFLEWYQQKPGKAPKLLIYFTSRLRHGVPS
RFSGSGSGTDFTLTISSLQPEDFATYYCLQNVANPATFSQGTKVEIKR 1h-239-891(S9C) (SEQ ID NO: 6):
DIQMTQSPCSLSASVGDRVTITCRASRPIWPFLEWYQQKPGKAPKLLIYFTSRLRHGVPS
RFSGSGSGTDFTLTISSLQPEDFATYYCLQNVANPATFSQGTKVEIKR 1h-239-891(R18C) (SEQ ID NO: 7):
DIQMTQSPSSLSASVGDCVTITCRASRPIWPFLEWYQQKPGKAPKLLIYFTSRLRHGVPS
RFSGSGSGTDFTLTISSLQPEDFATYYCLQNVANPATFSQGTKVEIKR 1h-239-891(G41C) (SEQ ID NO: 8):
DIQMTQSPSSLSASVGDRVTITCRASRPIWPFLEWYQQKPCKAPKLLIYFTSRLRHGVPS
RFSGSGSGTDFTLTISSLQPEDFATYYCLQNVANPATFSQGTKVEIKR 1h-239-891(K42C) (SEQ ID NO: 9):
DIQMTQSPSSLSASVGDRVTITCRASRPIWPFLEWYQQKPGCAPKLLIYFTSRLRHGVPS
RFSGSGSGTDFTLTISSLQPEDFATYYCLQNVANPATFSQGTKVEIKR 1h-239-891(K45C) (SEQ ID NO: 10):
DIQMTQSPSSLSASVGDRVTITCRASRPIWPFLEWYQQKPGKAPCLLIYFTSRLRHGVPS
RFSGSGSGTDFTLTISSLQPEDFATYYCLQNVANPATFSQGTKVEIKR 1h-239-891(S60C) (SEQ ID NO: 11):
DIQMTQSPSSLSASVGDRVTITCRASRPIWPFLEWYQQKPGKAPKLLIYFTSRLRHGVPC
RFSGSGSGTDFTLTISSLQPEDFATYYCLQNVANPATFSQGTKVEIKR 1h-239-891(D70C) (SEQ ID NO: 12):
DIQMTQSPSSLSASVGDRVTITCRASRPIWPFLEWYQQKPGKAPKLLIYFTSRLRHGVPS
RFSGSGSGTCFTLTISSLQPEDFATYYCLQNVANPATFSQGTKVEIKR 1h-239-891(T74C) (SEQ ID NO: 13):
DIQMTQSPSSLSASVGDRVTITCRASRPIWPFLEWYQQKPGKAPKLLIYFTSRLRHGVPS
RFSGSGSGTDFTLCISSLQPEDFATYYCLQNVANPATFSQGTKVEIKR 1h-239-891(Q79C) (SEQ ID NO: 14):
DIQMTQSPSSLSASVGDRVTITCRASRPIWPFLEWYQQKPGKAPKLLIYFTSRLRHGVPS
RFSGSGSGTDFTLTISSLCPEDFATYYCLQNVANPATFSQGTKVEIKR 1h-239-891(K103C) (SEQ ID NO: 15):
DIQMTQSPSSLSASVGDRVTITCRASRPIWPFLEWYQQKPGKAPKLLIYFTSRLRHGVPS
RFSGSGSGTDFTLTISSLQPEDFATYYCLQNVANPATFSQGTCVEIKR
```

In certain specific embodiments, the anti-CD28 domain antibody may comprise 1h-239-891(D70C) (SEQ ID NO: 543). The anti-CD28 domain antibody may comprise a 40 kDa branched polyethylene glycol. The anti-CD28 domain antibody can be BMS-931699. For example, BMS-931699 is a potent inhibitor of T cell proliferation and cytokine production, with an $EC_{50}$ of 35±14 ng/mL and 25±6 ng/mL, respectively. BMS-908613-P40B (a macaque surrogate for BMS-931699) is equipotent at inhibiting both CD80- and CD86-driven T cell proliferation. Importantly, no agonist or co-agonist activity, as measured by T cell proliferation or cytokine release, was observed with BMS-931699.

In one embodiment, the binding of the domain antibody to CD28 does not substantially agonize CD28 activity. In particular, the dAb does not agonize CD28 signaling in combination with T cell receptor signaling. In another embodiment, the domain antibody inhibits the binding of CD28 to CD80. In another embodiment, the domain antibody inhibits the binding of CD28 to CD80, and does not substantially agonize signaling by CD28. In yet another embodiment, the domain antibody inhibits the binding of CD28 to CD86. In another embodiment, the domain antibody inhibits the binding of CD28 to CD86, and does not substantially agonize signaling by CD28.

In an aspect, the dAb does not substantially induce T cell proliferation in combination with T cell receptor signaling. In another aspect, the dAb does not substantially induce cytokine secretion by T cells in combination with T cell receptor signaling. In an embodiment, a cytokine is at least one cytokine selected from the group consisting of GM-CSF, IL-2, IL-3, IL-4, IL-5, IL-6, IL-10, IL-12 IL-13, IL-15, IL-17, IL-21, IL-22, IL-24, TGFβ, TNF-α, TNF-β, IFN-α, IFN-β, IFN-γ.

In one aspect, because human antibodies will avoid the generation of an immune response to the antibodies when administered to human subjects for the treatment or prevention of disease, the domain antibody is a human domain antibody that monovalently binds CD28, and in an exemplary embodiment, without substantially agonizing CD28 activity.

In one embodiment, the domain antibody interacts with human CD28 with a $K_d$ in the range of 50 nM to 1 pM, inclusive, as measured by surface plasmon resonance. For example, the $K_d$ for human CD28 can be 25 nM to 20 pM, 10 nM to 20 pM, 5 nm to 20 pM, 1 nM to 20 pM, 0.5 nM to 20 pM, 0.1 nM to 20 pM, 0.1 nM to 50 pM, 75 pM to 20 pM, or even 50 pM to 20 pM. In an embodiment, the $K_d$ for human CD28 is about 50 pM.

In one embodiment, the domain antibody inhibits binding of CD80 to CD28 with an $EC_{50}$ of 50 nM or less. In one embodiment, the domain antibody inhibits binding of CD86 to CD28 with an $EC_{50}$ of 50 nM or less. In a further embodiment, the domain antibody has binding specificity to CD28 with a $K_{off}$ rate constant of $1 \times 10^{-3}$ $s^{-1}$ or less, $1 \times 10^{-4}$ $s^{-1}$ or less, $1 \times 10^{-5}$ $s^{-1}$ or less, or $1 \times 10^{-6}$ $s^{-1}$ or less, as determined by surface plasmon resonance. In one embodiment, the domain antibody neutralizes CD28 in a standard assay with a $EC_{50}$ of 50 nM or less.

In another embodiment, the domain antibody comprises a single immunoglobulin variable domain that binds CD28. In one embodiment, the single immunoglobulin variable domain is a $V_H$ or a $V_L$ domain. In another embodiment, the domain antibody comprises a homomultimer or heteromultimer of two variable domains, e.g., a $V_H$ and $V_L$ domain, but one of the variable domains has the capacity to bind CD28 without the need for a corresponding $V_L$ or $V_H$ domain. That is, the dAb binds an antigen independently of the additional $V_H$ or $V_L$ domains. The variable domains in these embodiments may comprise three complementarity determining regions (CDRs). In another embodiment, the domain antibody is free of an Fc domain. The limits of an Fc domain are set out in Kabat et al. (1991, Sequences of Immunological Interest, 5th ed. U.S. Dept. Health & Human Services, Washington, D.C.; incorporated herein by reference). In the alternative, an Fc domain consists of the CH2-CH3 regions, optionally including a hinge region linked to the CH2.

In one aspect, the domain antibody comprises a universal framework. In this aspect, a domain antibody may comprise one or more framework regions comprising an amino acid sequence that is the same as the amino acid sequence of a corresponding framework (FW) region encoded by a human germline antibody gene segment, or the amino acid sequence of one or more of said framework regions collectively comprising up to 5, e.g., 1, 2, 3, 4 or 5, amino acid differences relative to the amino acid sequence of said corresponding framework region encoded by a human germline antibody gene segment.

In one embodiment, the dAb comprises amino acid sequences of FW1, FW2, FW3, and FW4 that correspond to the FW1, FW2, FW3, and FW4 of a human antibody, e.g., a human germline antibody. In a further embodiment, some or all of the amino acid sequences of FW1, FW2, FW3, and FW4 of the domain antibody are the same as the amino acid sequences of corresponding framework regions encoded by human germline antibody gene segments. For example, FW2 may be identical to the FW2 of a human antibody. In another embodiment, the amino acid sequences of FW1, FW2, FW3, and FW4 collectively contain up to 10 amino acid differences relative to the amino acid sequences of corresponding framework regions encoded by said human germline antibody gene segment. In a further embodiment of the foregoing, the human germline antibody gene segment can be selected from the group consisting of DP47, DP45, DP48, and DPK9. In one embodiment, the universal framework comprises a $V_H$ framework selected from the group consisting of DP47, DP45, and DP38, and/or the $V_L$ framework is DPK9.

In one aspect, a domain antibody is formatted to increase its in vivo half-life. In particular, the domain antibody has an increased in vivo t-α or t-β half-life relative to the same unformatted domain antibody.

In one embodiment, the tα-half-life of the domain antibody composition is increased by 10% or more when compared to an unmodified protein assayed under otherwise identical conditions. In another embodiment, the tα-half-life of the domain antibody composition is increased by 50% or more. In another embodiment, the tα-half-life of the domain antibody composition is increased by 2× or more. In another embodiment, the tα-half-life of the domain antibody composition is increased by 5× or more, e.g., 10×, 15×, 20×, 25×, 30×, 40×, 50×, or more. In another embodiment, the tα-half-life of the domain antibody composition is increased by 100×, 200×, 300×, 400×, 500×, or more.

In another embodiment, the domain antibody has a tα half-life of 0.25 to 6 hours, inclusive. In another embodiment, the tα half-life is in the range of 30 minutes to 12 hours, inclusive. In another embodiment, the tα-half-life of the domain antibody is in the range of 1 to 6 hours.

In another embodiment, the tβ-half-life of the domain antibody is increased by 10% or more when compared to an unmodified protein assayed under otherwise identical conditions. In another embodiment, the tβ-half-life of the domain antibody is increased by 50% or more. In another embodiment, the tβ-half-life of the antibody domain antibody is increased by 2× or more. In another embodiment, the tβ-half-life of the domain antibody is increased by 5× or more, e.g., 10×, 15×, 20×, 25×, 30×, 40×, or more. In another embodiment, the tβ-half-life of the domain antibody is increased by 50× or more.

In another embodiment, the domain antibody has a tβ half-life of 1 hour to 744 hours, inclusive. In another embodiment, the tβ-half-life is in the range of 12 to 48 hours, inclusive. In another embodiment, the tβ half-life is in the range of 12 to 26 hours, inclusive. In yet another embodiment, the tβ half-life is about 336 hours.

In addition to, or alternative to the above criteria, a domain antibody-containing composition is provided comprising a ligand having an AUC value (area under the curve) in the range of 1 mg min/ml or more. In one embodiment, the lower end of the range is 5, 10, 15, 20, 30, 100, 200, or 300 mg min/ml. In addition, or alternatively, a ligand or composition has an AUC in the range of up to 600 mg min/ml. In one embodiment, the upper end of the range is 500, 400, 300, 200, 150, 100, 75, or 50 mg min/ml. Advantageously a ligand will have an AUC in the range selected from the group consisting of the following: 15 to 150 mg min/ml, 15 to 100 mg min/ml, 15 to 75 mg min/ml, and 15 to 50 mg min/ml.

In another embodiment, the formatting comprises PEGylation of the dAb. In one embodiment, the PEG is covalently linked. In another embodiment, the PEG is linked to the domain antibody at a cysteine or lysine residue. In yet another embodiment, the PEG-linked domain antibody has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

In another embodiment, the PEG-linked domain antibody has an increased in vivo half-life relative to the same polypeptide composition lacking linked polyethylene glycol. In another embodiment, the tα-half-life of the domain antibody composition is increased by 10% or more. In another embodiment, the tα-half-life of the domain antibody composition is increased by 50% or more. In another embodiment, the tα-half-life of the domain antibody composition is increased by 2× or more. In another embodiment, the tα-half-life of the domain antibody composition is increased by 5× or more, e.g., 10×, 15×, 20×, 25×, 30×, 40×, 50×, or more. In another embodiment, the tα-half-life of the domain antibody composition is increased by 100×, 200×, 300×, 400×, 500×, or more.

In another embodiment, the PEG-linked domain antibody has a tα half-life of 0.25 to 6 hours, inclusive. In another embodiment, the tα half-life is in the range of 30 minutes to 12 hours, inclusive. In another embodiment, the tα-half-life of the domain antibody is in the range of 1 to 6 hours.

In another embodiment, the tβ-half-life of the PEG-linked domain antibody is increased by 10% or more. In another embodiment, the tβ-half-life of the PEG-linked domain antibody is increased by 50% or more. In another embodiment, the tβ-half-life of the PEG-linked domain antibody is increased by 2× or more. In another embodiment, the tβ-half-life of the PEG-linked domain antibody is increased by 5× or more, e.g., 10×, 15×, 20×, 25×, 30×, 40×, or more. In another embodiment, the tβ-half-life of the PEG-linked domain antibody is increased by 50× or more.

In another embodiment, the PEG-linked domain antibody has a tβ half-life of 1 to 170 hours, inclusive. In another embodiment, the tβ-half-life is in the range of 12 to 48 hours, inclusive. In another embodiment, the tβ-half-life is in the range of 12 to 26 hours, inclusive.

In another embodiment, the PEG-linked domain antibody has an AUC value (area under the curve) in the range of 1 mg·min/ml or more. In one embodiment, the lower end of the range is about 5, 10, 15, 20, 30, 100, 200, or 300 mg min/ml. In addition, or alternatively, a ligand or composition has an AUC in the range of up to about 600 mg min/ml. In one embodiment, the upper end of the range is about 500, 400, 300, 200, 150, 100, 75, or 50 mg min/ml. Advantageously a ligand will have an AUC in the range selected from the group consisting of the following: about 15 to 150 mg min/ml, about 15 to 100 mg min/ml, about 15 to 75 mg min/ml, and about 15 to 50 mg min/ml.

The dAb may inhibit binding of CD28 to CD80 and/or CD86 with an $EC_{50}$ of about 100 nM, about 50 nM, about 1 nM, about 500 pM, about 100 pM, about 50 pM, about 10 pM, about 5 pM, or about 1 pM. For example, the domain antibody inhibits binding of CD28 to CD80 with an $EC_{50}$ in the range of 1 pM to 1.5 µM, inclusive; $EC_{50}$ for inhibition of CD28 binding to CD80. The $EC_{50}$ can be in the range of 1 pM to 1 µM, 1 pM to 900 nM, 1 pM to 800 nM, 1 pM to 700 nM, 1 pM to 600 nM, 1 pM to 500 nM, 1 pM to 400 nM, 1 pM to 300 nM, 1 pM to 200 nM, 1 pM to 100 nM, 1 pM to 50 nM, 1 pM to 10 nM, 1 pM to 1 nM, 1 pM to 500 pM, 1 pM to 100 pM, 1 pM to 50 pM, 1 pM to 10 pM, or 1 pM to 5 pM. Further acceptable ranges include, for example, 50 pM to 1 µM, 100 pM to 500 nM, 125 pM to 250 nM, 150 pM to 200 nM, 150 pM to 100 nM, and 200 pM to 50 nM.

In another embodiment, the domain antibody inhibits binding of CD28 to CD86 with an $EC_{50}$ in the range of 1 pM to 1.5 µM, inclusive; $EC_{50}$ for inhibition of CD28 binding to CD86. The $EC_{50}$ can be in the range of 1 pM to 1 µM, 1 pM to 900 nM, 1 pM to 800 nM, 1 pM to 700 nM, 1 pM to 600 nM, 1 pM to 500 nM, 1 pM to 400 nM, 1 pM to 300 nM, 1 pM to 200 nM, 1 pM to 100 nM, 1 pM to 50 nM, 1 pM to 10 nM, 1 pM to 1 nM, 1 pM to 500 pM, 1 pM to 100 pM, 1 pM to 50 pM, 1 pM to 10 pM, or 1 pM to 5 pM. Further acceptable ranges include, for example, 50 pM to 1 µM, 100 pM to 500 nM, 125 pM to 250 nM, 150 pM to 200 nM, 150 pM to 100 nM, and 200 pM to 50 nM.

The domain antibody may comprise one or more framework regions comprising an amino acid sequence that is the same as the amino acid sequence of a corresponding framework region encoded by a human germline antibody gene segment, or the amino acid sequence of one or more of said framework regions collectively comprises up to 5 amino acid differences relative to the amino acid sequence of said corresponding framework region encoded by a human germline antibody gene segment.

In one embodiment, the amino acid sequences of FW1, FW2, FW3, and FW4 of the domain antibody are the same as the amino acid sequences of corresponding framework regions encoded by a human germline antibody gene segment, or the amino acid sequences of FW1, FW2, FW3, and FW4 collectively contain up to 10 amino acid differences relative to the amino acid sequences of corresponding framework regions encoded by said human germline antibody gene segment.

In one embodiment, the amino acid sequences of said FW1, FW2, and FW3 of the domain antibody are the same as the amino acid sequences of corresponding framework regions encoded by human germline antibody gene segments. The human germline antibody gene segments may be selected from the group consisting of DP47, DP45, DP48, and DPK9.

3. Uses of Domain Antibodies

Domain antibodies as described herein are useful for antagonizing the activity of CD28. Therefore, domain antibodies as described herein can be used to treat a patient having a condition, disease or disorder mediated in whole or in part by CD28 activity. For example, domain antibodies as described herein are useful for the treatment or prevention of diseases or disorders in which inappropriate activation of a CD28-mediated pathway is involved, such as systemic lupus erythematosus (SLE).

As used herein "treat", "reduce", "prevent", or "alleviate" as it relates to a symptom of disease refer to a decrease of a symptom by at least 10% based on a clinically measurable parameter, or by at least one point on a clinically-accepted scale of disease or symptom severity. As used herein, the term "symptom(s) of systemic lupus erythematosus" refers to any of the clinically relevant symptoms of SLE known to those of skill in the art, including, but not limited to, BICLA (BILAG-Based Composite Lupus Assessment), SRI (Systemic Lupus Erythematosus Responder Index). Non-limiting examples include the accumulation of IgG autoantibodies (e.g., against nuclear antigens such as chromatin, snRNPs (especially U1, Sm, Ro/SSA and La/SSB), phospholipids and cell surface molecules), hemolytic anemia, thrombocytopenia, leukopenia, glomerulonephritis, vasculitis, arthritis, and serositis). A reduction in such a symptom of a patient is a reduction by at least 10% in a clinically measurable parameter, or by at least one point on a clinically-accepted scale of disease severity, compared to a patient treated with a placebo.

In an aspect, autoimmune diseases frequently involve inappropriate regulation or activity of CD28 pathways. Administration of a domain antibody as described herein to an individual suffering from such a disease, including an autoimmune disease, can reduce one or more symptoms of the disease. Non-limiting examples of diseases for which the domain antibodies described herein can be therapeutically useful include, but are not limited to, Addison's disease, allergy, ankylosing spondylitis, asthma, atherosclerosis, autoimmune diseases of the ear, autoimmune diseases of the eye, autoimmune atrophic gastritis, autoimmune hepatitis, autoimmune hymolytic anemia, autoimmune parotitis, primary biliary cirrhosis, benign lymphocytic aniitis, colitis, coronary heart disease, Crohn's disease, diabetes (Type I), diabetes, including Type 1 and/or Type 2 diabetes, epididymitis, glomerulonephritis, Goodpasture's syndrome, Graves' disease, Guillain-Barre syndrome, Hashimoto's disease, hemolytic anemia, idiopathic thrombocytopenic purpura, inflammatory bowel disease (IBD), immune response to recombinant drug products, e.g., factor VII in hemophilia, systemic lupus erythematosus, lupus nephritis, male infertility, mixed connective tissue disease, multiple sclerosis, myasthenia gravis, primary myxedema, pemphigus, pernicious anemia, polymyositis, psoriasis, psoriatic arthritis, rheumatic fever, rheumatoid arthritis, sarcoidosis, scleroderma, Sjogren's syndrome, spondyloarthropathies, sympathetic ophthalmia, T-cell lymphoma, T-cell acute lymphoblastic leukemia, testicular antiocentric T-cell lymphoma, thyroiditis, transplant rejection, ulcerative colitis, autoimmune uveitis, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, and alcohol and drug addiction.

The domain antibodies described herein also can be therapeutically useful in graft-related diseases, such as graft versus host disease (GVHD), acute transplantation rejection, and chronic transplantation rejection.

In certain embodiments, the present invention provides a method of treating an immune disease in a patient, comprising administering to the patient a therapeutically effective amount of an anti-CD28 domain antibody. To illustrate, the immune disease may be systemic lupus erythematosus. The patient receiving an anti-CD28 domain antibody may have decreased SLE symptoms compared to a patient receiving placebo. For example, the patient receiving an anti-CD28 domain antibody may have lower levels of C3, C4, anti-dsDNA, and/or anti-ANA compared to a patient receiving placebo. For example, the patient receiving an anti-CD28 domain antibody may have decreased arthritis symptoms compared to a patient receiving placebo. For example, the patient receiving an anti-CD28 domain antibody may have decreased inflammatory skin disease symptoms compared to a patient receiving placebo.

The treatment may further comprise administering an immunosuppressive/immunomodulatory and/or anti-inflammatory agent. The treatment may be administered in combination with an immunosuppressive/immunomodulatory and/or anti-inflammatory agent. Such additional immunosuppressive/immunomodulatory and/or anti-inflammatory agents or therapies may comprise calcineuirin inhibitor, cyclosporine, cytoxan, prednisone, azathioprine, methotrexate, corticosteroids, nonsteroidal antiinflammatory drugs/Cox-2 inhibitors, hydroxychloroquine, sulphasalazopryine, gold salts, etanercept, infliximab, anakinra, mizoribine, mycophenolic acid, mycophenolate mofetil, interferon beta-1a, interferon beta-1b, glatiramer acetate, mitoxantrone hydrochloride, and/or other biologics like anti-TNF. The domain antibodies also may be administered in combination with one or more of the following agents to regulate an immune response: CTLA4, soluble gp39 (also known as CD40 ligand (CD40L), CD154, T-BAM, TRAP), soluble CD29, soluble CD40, soluble CD80, soluble CD86, soluble CD56, soluble Thy-1, soluble CD3, soluble TCR, soluble VLA-4, soluble VCAM-1, soluble LECAM-1, soluble ELAM-1, soluble CD44, antibodies reactive with gp39, antibodies reactive with CD40, antibodies reactive with B7, antibodies reactive with CD28, antibodies reactive with LFA-1, antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-2), antibodies reactive with CTLA4, antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44, monoclonal antibodies to leukocyte receptors, e.g., MHC, CD2, CD3, CD4, CD11a/CD18, CD7, CD25, CD 27, B7, CD40, CD45, CD58, CD 137, ICOS, CD150 (SLAM), OX40, 4-1BB or their ligands.

Where domain antibodies of the invention are administered in combination with another immunosuppressive/immunomodulatory or anti-inflammatory agent or therapy, e.g., as specified above, the administration may be made concomitantly or in sequence. When the dAbs are administered concomitantly with another agent, such as an agent specified above, the dAb and agent may administered in the same pharmaceutical composition.

The treatment may produce at least one therapeutic effect measurable by a biomarker selected from the group consisting of: CD28 receptor occupancy on T cells, C3, C4, anti-dsDNA, anti-ANA, anti-Ro autoantibodies, anti-La autoantibodies, anti-RNP autoantibodies, anti-Sm autoantibodies, anti-APL autoantibodies, CRP, total IgG, total IgM, RNA transcripts in whole blood, NGAL in urine, TWEAK in urine, MCP-1 in urine, IL-18 in urine, IL-1 in urine, total soluble CD28, T cell activation, leukocyte surface CD4, leukocyte surface CD8, leukocyte surface CD28, leukocyte surface CD57 and leukocyte intracellular granzyme B, serum IL-6, serum IL-18, serum TNF-α, serum α-interferon, serum BLyS(BAFF), CD154, sCD28 and microvessicles.

4. Pharmaceutical Compositions, Dosage, and Administration

The anti-CD28 domain antibodies set forth herein can be incorporated into pharmaceutical compositions suitable for administration to a subject. Typically, the pharmaceutical composition comprises the domain antibody and a pharmaceutically acceptable carrier. As used herein, "pharmaceutically acceptable carrier" includes any and all solvents, dispersion media, coatings, antibacterial, and antifungal agents, isotonic and absorption delaying agents, and the like that are physiologically compatible. The term "pharmaceutically acceptable carrier" excludes tissue culture medium comprising bovine or horse serum. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances include minor amounts of auxiliary substances such as wetting or emulsifying agents, preservatives or buffers, which enhance the shelf life or effectiveness of the domain antibody.

The compositions as described herein may be in a variety of forms. These include, for example, liquid, semi-solid, and solid dosage forms, such as liquid solutions (e.g., injectable and infusible solutions), dispersions or suspensions, powders, liposomes, and suppositories. The preferred form depends on the intended mode of administration and therapeutic application. Typical preferred compositions are in the form of injectable or infusible solutions, such as compositions similar to those used for passive immunization of humans with other antibodies. One mode of administration is parenteral (e.g., intravenous, subcutaneous, intraperitoneal, intramuscular).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

The domain antibodies described herein can be administered by a variety of methods known in the art, although for many therapeutic applications. The polypeptide can be administered by intravenous (IV), intramuscular (IM) or subcutaneous (SC) injection.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, and microencapsulated delivery systems. Domain antibodies are well suited for formulation as extended release preparations due, in part, to their small size, the number of moles per dose can be significantly higher than the dosage of, e.g., full sized antibodies. Biodegradable, biocompatible polymers can be used, such as ethylene vinyl acetate, polyanhydrides, polyglycolic acid, collagen, polyorthoesters, and polylactic acid. Prolonged absorption of injectable compositions can be brought about by including in the composition an agent that delays absorption, for example, monostearate salts and gelatin. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. Additional methods applicable to the controlled or extended release of polypeptide agents such as the monovalent domain antibodies disclosed herein are described, for example, in U.S. Pat. Nos. 6,306,406 and 6,346,274, as well as, for example, in U.S. Patent Publication Nos. US20020182254 and US20020051808, all of which are incorporated herein by reference for all purposes. For example, the domain antibody can be formulated in a pharmaceutical composition for subcutaneous administration, which can include a pharmaceutically acceptable carrier. The pharmaceutical composition can further comprise 12.5 mg/mL BMS-931699 in 20 mM phosphate, pH 5.9, with 5% (w/v) sorbitol.

Additional active compounds can also be incorporated into the compositions. In certain embodiments, a domain antibody is co-formulated with and/or co-administered with one or more additional therapeutic agents. For example, a domain antibody can be co-formulated and/or co-administered with one or more additional antibodies that bind other targets (e.g., antibodies that bind other cytokines or that bind cell surface molecules), or, for example, one or more cytokines. Such combination therapies may utilize lower dosages of the administered therapeutic agents, thus avoiding possible toxicities or complications associated with the various monotherapies.

The pharmaceutical compositions disclosed herein can include a "therapeutically effective amount" or a "prophylactically effective amount" of a domain antibody. A "therapeutically effective amount" refers to an amount effective, at dosages and for periods of time necessary, to achieve the desired therapeutic result. A therapeutically effective amount of the domain antibody can vary according to factors such as the disease state, age, sex, and weight of the individual, and the ability of domain antibody to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

A non-limiting range for a therapeutically or prophylactically effective amount of a domain antibody is 0.1-20 mg/kg, and in an aspect, 1-10 mg/kg. For example, the domain antibody can be administered at a dose of about 1.25 mg to about 12.5 mg; i.e. the dose can be at least 1.25 mg, at least 5 mg, at least 12.5 mg, about 1.25 mg, about 5 mg, or about 12.5 mg. 1.25 mg to about 12.5 mg mg of domain antibody can be administered subcutaneously. The dose may be administered on a fixed or varied schedule. For example, the dose may be administered on a weekly or bi-weekly basis. The dose can be administered over a set treatment regimen, such as once every two weeks for 24 weeks (12 doses total) or once a week for 24 weeks (24 doses total). It is to be noted that dosage values can vary with the type and severity of the condition to be alleviated. It is to be further understood that for any particular subject, specific dosage regimens should be adjusted over time according to the individual need and the professional judgment of the administering clinician.

The efficacy of treatment with a domain antibody as described herein is judged by the skilled clinician on the basis of improvement in one or more symptoms or indicators of the disease state or disorder being treated. An improvement of at least 10% (increase or decrease, depending upon the indicator being measured) in one or more clinical indicators is considered "effective treatment," although greater improvements are included, such as about 20%, 30%, 40%, 50%, 75%, 90%, or even 100%, or, depending upon the indicator being measured, more than 100% (e.g., two-fold, three-fold, ten-fold, etc., up to and including attainment of a disease-free state. Indicators can be physical measurements, e.g., enzyme, cytokine, growth factor or metabolite levels, rate of cell growth or cell death, or the presence or amount of abnormal cells. One can also measure, for example, differences in the amount of time between flare-ups of symptoms of the disease or disorder (e.g., for remitting/relapsing diseases, such as multiple sclerosis). Alternatively, non-physical measurements, such as a reported reduction in pain or discomfort or other indicator of disease status can be relied upon to gauge the effectiveness of treatment. Where non-physical measurements are made, various clinically acceptable scales or indices can be used, for example, the Crohn's Disease Activity Index, or CDAI (Best et al. (1976) Gastroenterology 70: 439), which combines both physical indicators, such as hematocrit and the number of liquid or very soft stools, among others, with patient-reported factors such as the severity of abdominal pain or cramping and general well-being, to assign a disease score.

As the term is used herein, "prophylaxis" performed using a composition as described herein is "effective" if the onset or severity of one or more symptoms is delayed or reduced by at least 10%, or abolished, relative to such symptoms in a similar individual (human or animal model) not treated with the composition.

Whereas the domain antibodies described herein bind human CD28, where one is to evaluate its effect in an animal model system, the polypeptide must cross-react with one or more antigens in the animal model system, in an aspect, at high affinity. One of skill in the art can readily determine if this condition is satisfied for a given animal model system and a given domain antibody. If this condition is satisfied, the efficacy of the domain antibody can be examined by administering it to an animal model under conditions which mimic a disease state and monitoring one or more indicators of that disease state for at least a 10% improvement.

EXAMPLES

Example 1: Pharmacokinetics of PEGylated 1h-239-891 (D70C) in Cynomolgus Monkeys Studies were performed in the cynomolgus monkeys to evaluate the pharmacokinetics of 1h-239-891(D70C) PEGylated with a 30 kDa linear (P30L) or a 40 kDa branched PEG (P40B), following single intravenous (IV) doses of 0.05 and 5 mg/kg, or subcutaneous (SC) doses of 0.05, 0.5 and 5 mg/kg (mpk).

Tables 1 and 2 summarize the IV and SC PK parameters of 1h-239-891(D70C)-P30L and -P40B, respectively. Non-linear pharmacokinetics were observed for both P30L and P40B PEG formats. The terminal half-lives (T½) of P30L and P40B were 1.6 and 2.5 days, respectively. The absorption of 1h-239-891(D70C) was nearly complete after SC dosing for P30L at 0.05 mg/kg and for P40B at 0.05 and 5 mg/kg (bioavailability F>90%), but reduced to 70% for P30L at 5 mg/kg. The steady-state volume of distribution (Vss) was comparable between the two PEG formats. However, the systemic clearance (CL) of P40B was 3-fold lower than that of 30 L, largely accounting for differences in the AUC and T½ observed between the two formats. At 0.05 mg/kg, for example, T½ could not be accurately determined because the drug concentration at the terminal phase was below the level of quantitation (LLQ).

TABLE 1

PK Parameters of 1h-239-891(D70C)-P30L

| | | iv | | | | sc | | |
|---|---|---|---|---|---|---|---|---|
| Dose | mpk | 0.05 (n = 1) | 5 (n = 1) | Dose | mpk | 0.05 (n = 2) | 0.5 (n = 3) | 5 (n = 2) |
| $AUC_{tot}$ | nM*h | 996 | 182161 | $C_{max}$ | nMolar | 21 | 225 | 1980 |
| $T_{1/2}$ | h | nd* | 39 | $T_{max}$ | h | 8 | 8 | 16 |
| MRT | h | 15.3 | 20.1 | $AUC_{tot}$ | nM*h | 905 | 12774 | 125742 |
| CL | mL/min/kg | 0.069 | 0.038 | $T_{1/2}$ | h | 33 | 34 | 36 |
| $V_{ss}$ | L/kg | 0.063 | 0.045 | MRT | h | 48 | 56 | 56 |
| | | | | F | % | 91 | | 69 |

*Cannot be accurately determined because drug concentrations at the terminal phase were below LLQ.

TABLE 2

PK Parameters of 1h-239-891(D70C)-P40B

| | | iv | | | | sc | | |
|---|---|---|---|---|---|---|---|---|
| Dose | mpk | 0.05 (n = 1) | 5 (n = 1) | Dose | mpk | 0.05 (n = 2) | 0.5 (n = 3) | 5 (n = 2) |
| $AUC_{tot}$ | nM*h | 3704 | 499857 | $C_{max}$ | nMolar | 27 | 410 | 5075 |
| $T_{1/2}$ | h | 49 | 70 | $T_{max}$ | h | 36 | 27 | 36 |
| MRT | h | 61 | 65 | $AUC_{tot}$ | nM*h | 3561 | 52646 | 556918 |
| CL | mL/min/kg | 0.018 | 0.014 | $T_{1/2}$ | h | 56 | 65 | 61 |
| $v_{ss}$ | L/kg | 0.067 | 0.054 | MRT | h | 96 | 107 | 94 |
| | | | | F | % | 96 | | 100 |

*Cannot be accurately determined because drug concentrations at the terminal phase were below LLQ.

Example 2: BMS-931699 Surrogate Pharmacology

Surrogate CD28 dAbs that recognize mouse CD28, with potencies similar to BMS-931699, were used to evaluate the impact of direct inhibition of CD28 in murine efficacy models. In a mouse KLH antibody response model, BMS1m-74-14982-P40B (a murine surrogate for BMS-931699) completely suppressed IgG titers at 0.1 mg/kg in mice, with an in vivo $EC_{50}$ of 18 ng/mL. CD28 receptor occupancy (RO) of ~100% 24 hours post dose was required for maximal efficacy. In the same model, mCTLA4Ig completely suppressed the IgG response at 3 mg/kg, with an in vivo $EC_{50}$ of 1656 ng/mL.

Treatment with BMS1m-74-14982-P40B after disease onset (therapeutic mode) in the NZB/NZW F1 lupus model, was effective in reducing proteinuria, serum autoantibody titers, local cytokine gene expression, and glomerulonephritis/immune complex deposition. Most endpoints were fully impacted at the 0.5 mg/kg dose, with survival and anti-dsDNA requiring higher concentrations of 2 and 8 mg/kg, respectively. Taken as a whole, the in vitro and in vivo studies provide proof of concept for the dAb technology and confidence that a CD28 dAb should be efficacious in autoimmune diseases in the clinic.

The nonclinical safety assessment that supports the clinical development of BMS-931699 includes: 1) single-dose PK/PD studies conducted with BMS-908613-P40B in monkeys to support the minimal anticipated biological effect level (MABEL) dose rationale; 2) a single-dose exploratory toxicity study in mice with BMS1m-74-14982-S60C-P40B to assess potential toxicity of CD28 antagonism in a rodent model; 3) pivotal GLP 1- and 6-month repeat-dose toxicity studies of BMS-931699 in cynomolgus monkeys; 4) an exploratory in vitro study of potential BMS-931699-related effects (cytokine release, T-cell activation/proliferation) on human T cells; and 5) a Good Laboratory Practice (GLP) human tissue cross-reactivity study to demonstrate target distribution and inform of any potential unexpected epitope binding.

The cynomolgus monkey was selected as the toxicology species because BMS-931699 binds comparably to macaque CD28, is pharmacologically active in monkeys, and does not cross-react with rodent CD28.

Intended PD effects in cynomolgus monkeys have been demonstrated in vivo with BMS-908613-P40B (inhibition of TDARs) and with BMS-931699 (decreases in cortical lymphocytes in various lymph nodes which is reflective of decreased germinal center activity). In vitro, BMS-931699 and BMS-908613-P40B showed similar binding affinities for human CD28 and similar potency in in vitro mixed lymphocyte reaction (MLR) assays. The rodent surrogate of BMS-931699, BMS1m-74-14982-S60C-P40B, was used to assess the potential for toxicity in mice.

In the single-dose exploratory toxicity study in mice, BMS1m-74-14982-S60C-P40B at SC doses up to 18 mg/kg (AUC 5184 μg·h/mL) was not associated with any adverse drug-related findings. In the single-dose exploratory PK/PD studies in monkeys, BMS-908613-P40B at SC doses up to 5 mg/kg (AUC 6793 μg·h/mL) was not associated with any adverse drug-related findings including any effects on plasma cytokines. BMS-908613-P40B-related effects at doses ≥0.5 mg/kg were limited to reversible dose-dependent suppression of primary TDARs to KLH (IgG), when KLH was administered 24-hours postdose, an expected pharmacologic effect.

In a 5-week intermittent dose toxicity study in cynomolgus monkeys with a 8-week recovery, IV doses of BMS-931699 up to 15 mg/kg (combined sex mean AUC from time zero to 168 hours [AUC(0-168h)]≤16,700 μg·hr/mL) or a SC dose of 3.5 mg/kg (mean AUC 3520 μg·hr/mL) administered once weekly for 5 weeks were clinically well tolerated. Notably, BMS-931699-related effects at all doses (mean [AUC(0-168h)]≥1860 μg·h/mL on Day 22) included nonadverse reductions in peripheral blood regulatory T lymphocytes (Tregs), minimal to mild decreases in cortical lymphocytes in lymph nodes, and minimal to slight macrophage and/or epithelial cell vacuolation in various tissues that was not associated with inflammation or necrotic changes or altered organ function. Reductions in Tregs and cortical lymphocytes in lymph nodes were expected pharmacologic effects, while vacuolation in various tissues was attributed to the PEG moiety of BMS-931699. All BMS-931699-related effects showed partial to complete resolution following an 8-week recovery period with the exception of vacuolation in the choroid plexus epithelium and pituitary gland. Based on the low severity and lack of associated inflammatory or degenerative changes, the no-observed-adverse-effect level (NOAEL) was considered to be 15 mg/kg/week IV mean AUC[0-168h] of 15,200 g·h/mL on Day 22) and 3.5 mg/kg/week SC (mean AUC[0-168h] of 3330 μg·h/mL on Day 22).

In a 6-month intermittent dose toxicity study with a 6-month recovery, BMS-931699 was clinically well tolerated by cynomolgus monkeys for 6 months when administered as weekly SC doses of ≤10 mg/kg (AUC[[0-168h] 12,100 μg·h/mL). The primary BMS-931699-related findings at all doses were pharmacologically-mediated decreases in peripheral blood Tregs, B lymphocytes, serum IgG, and cortical lymphocytes in lymph nodes or spleen. Given the changes in Tregs were minimal, reversible, and not associated with any other correlative adverse findings, they were not considered adverse. Other nonadverse microscopic findings at ≥1 mg/kg/week (AUC[0-168h] 1,350 g·h/mL) included PEG-related vacuolation of macrophages and/or epithelial cells in several tissues (choroid plexus of the brain, kidney, axillary lymph node, and injection sites), and increased thickness of the kidney interstitium. At ≥3.5 mg/kg/week (AUC[0-168h] of 4,450 μg·h/mL), PEG-related vacuolation of macrophages in the pituitary gland and increased incidence and severity of inflammation and hemorrhage at the subcutaneous injection sites were noted. Additional findings at 10 mg/kg/week included PEG-related vacuolation of macrophages in the mandibular and mesenteric lymph nodes, circumventricular organs of the brain, urinary bladder, ovaries, uterus, and spleen. All of the aforementioned findings showed evidence of reversibility (partial or complete) with the exception of increased thickness of the kidney interstitium and vacuolation of macrophages in the pituitary gland, circumventricular organs of the brain, urinary bladder, and uterus. These findings were not accompanied by degenerative or inflammatory changes and were considered not adverse. Lymphoma was noted in 1 female at 1 mg/kg/week that was considered secondary to BMS-931699-induced immunosuppression in cynomolgus monkeys latently infected with LCV; based on this finding a NOAEL was not determined in this study.

In both the single-dose exploratory PK and PD studies, and repeat-dose monkey toxicity studies, immunogenicity occurred with low incidence. Also, the presence of the anti-drug antibodies (ADAs) did not affect the PK, PD or toxicokinetics of BMS-931669 in monkeys. No adverse irritation or local intolerance was observed at the BMS-931699 IV or SC injection sites in either the 5-week or the 6-month studies in monkeys using BMS-931699 concentrations and injection rates greater than or equal to those recommended for human use. In an in vitro assay system, purified human T cells were incubated with BMS-931699 or the superagonist anti-CD28 monoclonal antibody (mAb) TGN 5.11A1 to monitor for potential effects on T-lymphocyte activation, proliferation, and cytokine release. There were no BMS-931699-related effects, while TGN 5.11A1 induced both cytokine release and cellular activation. In the GLP tissue-cross-reactivity study using a comprehensive panel of 23 human tissues, binding of BMS-931699 was limited to mononuclear cells in most human tissues. As CD28 is expressed primarily by T cells, the staining of blood lymphocytes and mononuclear cells throughout the human tissue panel was expected reactivity. Overall, BMS-931699 has demonstrated acceptable pharmacologic, nonclinical PK, PD, and toxicologic properties that support continued clinical development.

Evaluations of the potential effects of IV and/or SC administration of BMS-931699 on the cardiovascular, central/peripheral nervous, and/or respiratory systems were included as part of the pivotal GLP repeat-dose toxicity study in monkeys. Following 5-weekly IV/SC doses or 6-months of weekly IV doses of BMS-931699 in monkeys, clinical assessments yielded no findings for physical, neurologic, and ophthalmologic examinations; body temperature; heart rates; qualitative and quantitative electrocardiographic evaluations; respiratory rates; evaluations of lung sounds and mucous membrane color; and arterial oxygen saturation determinations, that were considered to be related to BMS-931699.

Example 3: Preclinical Metabolism and Pharmacokinetics

The PK of BMS1m-74-14982-S60C-P40Br and BMS-908613-P40Br, were evaluated in mice and cynomolgus monkeys, respectively. After intravenous (IV) administration (0.2 mg/kg in mice; 0.05, and 5 mg/kg in monkeys), circulating BMS-1m74-14982-S60C-P40B and BMS-908613-P40B concentrations exhibited bi-exponential declines. The steady-state volumes of distribution (Vss) for BMS1m-74-14982-S60C-P40B and BMS-908613-P40B in mice were (0.13 L/kg) which is greater than the reported plasma volume in mice indicating that the drug largely resides in the extracellular space. However, in monkeys, the Vss (0.053 L/kg) for BMS-908613-P40B was similar to the reported plasma volume, indicating very limited extravascular distribution. The serum clearance of BMS-1m74-14982-S60C-P40B in mice and plasma clearance of BMS-908613-P40B in monkeys were 3.9 mL/h/kg and 0.82 to 1.1 mL/h/kg, respectively. The apparent elimination half-life (T-HALF) after IV administration was 27 hours in mice and 50 to 71 hours in monkeys.

Following single SC administration (0.2 mg/kg in mice; 0.05, 0.5, and 5 mg/kg in monkeys), BMS-1m74-14982-S60C-P40B and BMS-908613-P40B were well absorbed, with bioavailability of 78% in mice and 96 to 111% in monkeys, respectively. The time of peak plasma or serum concentration (Tmax) was generally around 24 hours (range=8 to 36 hours). In a SC PK study (DS09012), BMS-908613-P40B exhibited a more than dose-proportional increase in exposure in female monkeys (at 0.05, 0.5, and 5 mg/kg, peak plasma concentrations [Cmax] were 0.335, 5.0, and 61.9 μg/mL, respectively, and the area under the concentration-time curve from time zero to infinity [AUC(INF)] values were 43.4, 642, and 6790 μg*h/mL, respectively). In a subsequent monkey SC PK/PD study (DS09013), in which monkeys were immunized with ovalbumin and KLH, linear PK was observed between 0.05 and 5 mg/kg in males, but, as in Study DS09012, there was a trend for a greater-than-proportional increase in exposure in females, but not in males.

Following intraperitoneal administration (0.08, 0.4, and 2 mg/kg) to mice, BMS 1m74-14982-S60C-P40Br exhibited an approximately dose-proportional increase in exposure. The Tmax was 4 to 9 hours.

Example 4: First-In-Humans Study: Clinical Pharmacology and Safety

The early clinical program for BMS-931699 consists of a First-in-Humans (FIH) single ascending dose (SAD) study (Part 1) along with a neo-antigen immunization SAD study (Part 2), followed by a multiple ascending dose (MAD) study in healthy subjects. A total of 156 subjects were enrolled in the FIH SAD study IM128001, including 108 subjects in Part 1 (single-ascending dose study) and 48 subjects in SAD Part 2 (KLH immunization). A total of 108 subjects received active study drug and 48 received placebo. In summary, BMS-931699 was safe and well tolerated after a single dose of up to 100 mg IV. There were no deaths. No clinically relevant changes in vital signs, physical findings, or ECGs were reported. No clinically meaningful changes in pro-inflammatory cytokines were observed following a single dose of BMS-931699 confirming the lack of CD28 receptor agonistic activity in humans. Two serious adverse events (SAEs) were reported, but both were considered to be unrelated to study drug. These included an event of acute pre-renal failure and an event of appendicitis. Acute infusion reactions occurred in 7 subjects; 3 of these events led to discontinuation of study drug prior to completion of infusion. All acute infusion reactions were moderate in intensity. Isolated asymptomatic alanine aminotransferase (ALT) increases were reported in both study drug-treated and placebo groups and no subject met Hy's criteria. The most frequent adverse effects (AEs) included headache, feeling hot, oropharyngeal pain, back pain, pruritus, and upper respiratory tract infection.

The MAD study IM128003 was performed in 24 subjects (3 cohorts of 8 subjects) treated for 5 weeks with either SC doses of BMS-931699 (6.25 mg every other week [EOW], 12.5 mg weekly [QW], or 37.5 mg QW) or placebo (3:1 randomization). As reported in the SAD study, preliminary results from the MAD study show no evidence of CD28 agonistic activity, as defined by clinically significant cytokine release and/or lymphocyte changes. Infections were observed in the BMS-931699-treated healthy subject cohorts (5/18; 27.8%) but no correlation was observed between exposure and infection rate.

In total, 6 infections were reported in 5 subjects, with 5 infections in 4 subjects considered related events. One subject, dosed at the 12.5 mg weekly regimen, experienced 2 infective episodes: oral herpes on study Day 40 followed after 7 days by upper respiratory infection, in both cases the severity was defined as mild. One subject, dosed at the 12.5 mg weekly schedule, presented with furuncle (mild severity) on study Day 69. One subject, dosed at 37.5 mg weekly, on Day 89 presented with a peritonsillar abscess of moderate severity, which required antibiotic treatment (500 mg amoxicillin three times a day [TID] for 10 days. One subject had a mild viral infection on Day 81 following administration of 37.5 mg BMS-931699 weekly, which was considered unrelated.

One subject had a SAE of severe cellulitis following administration of 6.25 mg every 2 weeks. The subject required hospitalization on Day 49 for cellulitis that developed in his right hand after damage of the skin at the base of his 3rd finger. When hospitalized, the patient was treated with IV antibiotics and the lesion was surgically drained. The SAE followed traumatic skin damage to his right hand, providing a breach of skin integrity for the development of cellulitis. However it could not be excluded that BMS-931699 might have made the subject more susceptible to the subsequent infection. Therefore the SAE was considered possibly related to the study drug.

Pharmacokinetics of BMS-931699
Pharmacokinetics Summary of IM128001: Single Ascending Dose Study The SAD study IM128001 evaluated BMS-931699 in the dose range of 0.01 mg to 100 mg (0.01, 0.05, 0.25, 3, 9, 25, 50, and 100 mg) following 30-minute IV infusion, and doses of 9, 25, and 50 mg following SC administration. BMS-931699 exhibited linear PK after single IV and SC administration. The Cmax and AUC(INF) of BMS-931699 administered IV and SC increased approximately in proportion to dose over the range of 3 mg to 100 mg. AUC and Cmax values of BMS-931699 increased in a dose-proportional manner following single doses of 3 mg to 100 mg IV and 9 mg to 50 mg SC in healthy subjects.

The mean total body clearance (CLT), Vz and Vss were in the range of 0.42-0.59 L/min, 3.4-5.1 L, and 3.2-4.5 L respectively, and relatively consistent among all the dose groups following single IV administration. The mean apparent total body clearance (CLT)/F and Vz/F were in the range of 0.59-0.70 L/min and 6.0-7.3 L, respectively, and relatively consistent among all the dose groups following single SC administration. The T-HALF of BMS-931699 was similar following a single dose or multiple doses in healthy subjects (4 to 5.5 days for single dose and 6 to 7 days for multiple doses). Bioavailability of BMS-931699 following SC administration on AUC(INF) was 68.2%.

Pharmacokinetics Summary of IM128003: Multiple Ascending Dose Study

The MAD study IM128003 evaluated BMS-931699 in three treatment groups: 6.25 mg every other week (3 doses), 12.5 mg weekly (5 doses), and 37.5 mg weekly (5 doses). Following every other week and weekly SC administration, the pharmacokinetics of BMS-931699 is linear over the range of 6.25 mg every other week to 37.5 mg weekly. The geometric mean of accumulation index of AUC were 1.3, 2.4 and 3 for 6.25 mg EOW, 12.5 mg QW and 37.5 mg QW, respectively.

Following multiple doses of BMS-931699, and a median T-HALF of 6 to 7 days were observed. The mean CL/F (0.345 to 0.46 L/min) is consistent with what was observed in SAD study. The reason of a slightly longer T-HALF reported in the MAD compared to the SAD study is likely due to the fact that more measurable concentration data at the terminal phase was available to estimate T-HALF of the BMS-931699 in the MAD study.

Example 5: Phase 2 Clinical Trials Dose Selection Rationale

Four treatments of BMS-931699 are selected for initial evaluation in humans in a Phase 2 dose ranging study, including 1.25 mg every other week, 5 mg every other week, 12.5 mg every other week, and 12.5 mg weekly. These dosing regimens were selected based on the PK/PD relationship using receptor occupancy (RO) and IgG suppression following Keyhole Limpet Hemocyacin (KLH)-antigen challenge as predictive markers for immunosuppressive activity and clinical efficacy in SLE patients.

Figure 4:
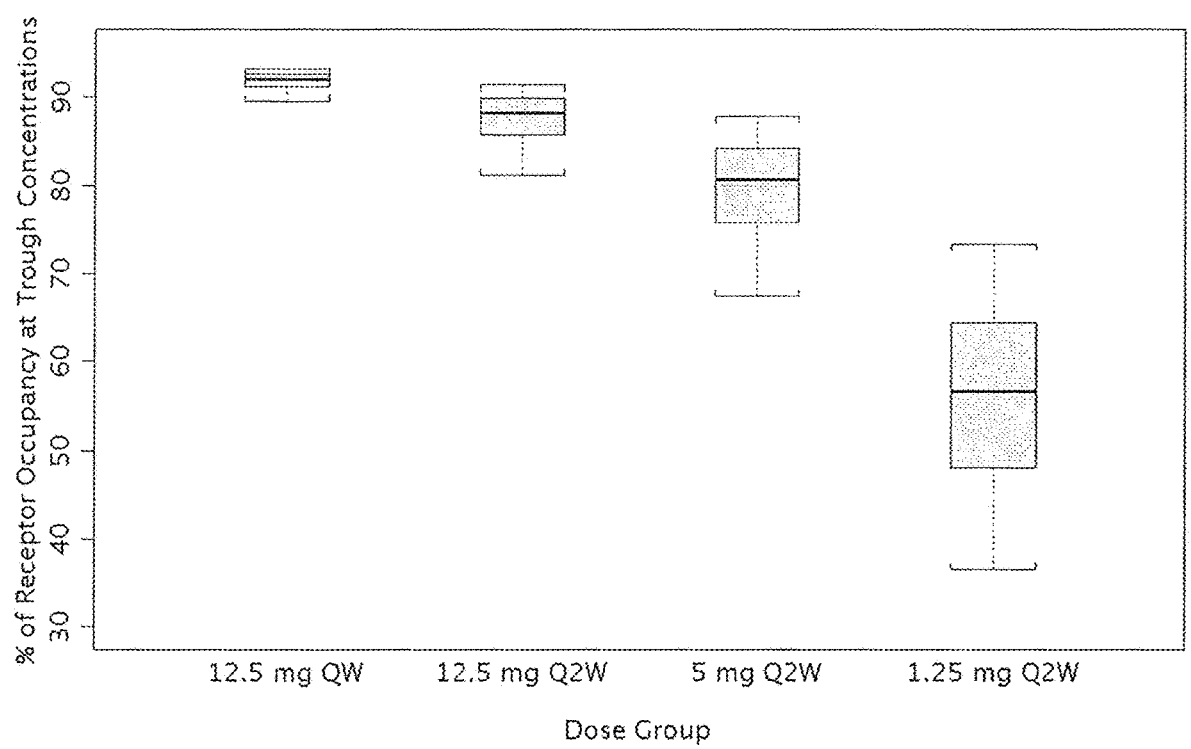
FIG. 4 demonstrates the expected receptor occupancy for BMS-931699 at steady state for 12.5 mg Weekly (QW), 12.5 mg Every 2 Weeks (QOW), 5 mg Every 2 Weeks (QOW) and 1.25 mg Every 2 Weeks (QOW).

Using the PK/PD model for receptor occupancy based on MAD data in humans, simulations were performed to identify dosing regimens that would provide a wide range of receptor occupancy to span the PK-receptor occupancy curve. These simulations predict that the 1.25 mg every other week, 5 mg every other week, 12.5 mg every other week, and 12.5 mg every week regimens provide approximately ≥40%, ≥70%, ≥80%, ≥90% receptor occupancy, respectively, throughout the dosing interval for majority of the patients (FIG. 4). The distribution of the receptor occupancy associated with the 1.25 mg every other week and 5 mg every other week regimen, fall on the steep portion of the PK-receptor occupancy curve, while the 12.5 mg every other week and every week regimens fall on the maximal plateau portion.

The preclinical monkey data suggested that >80% receptor occupancy for 2 weeks is needed for maximum immunosuppression as measured by IgG suppression following KLH-antigen challenge, and as levels of receptor fall below 80%, the immunosuppressive activity lessens and anti-KLH antibody formation rises. Results from the single ascending dose (SAD) study substantiate this premise. Near maximal IgG suppression was observed across treatment groups when approximately 80% receptor occupancy was achieved. Notably, in the lowest KLH treated group (9 mg), when the % RO declined below 80%, there was a subsequent rebound in IgG formation. Therefore, it is believed that high levels of target engagement, for example 80% receptor occupancy or greater, are needed to elicit immunosuppressive activity.

The exposures associated with the lowest proposed dose of 1.25 mg every other week dosing regimen are expected to be very low (5 times lower than the lowest dose tested in the MAD study in normal healthy volunteers) with a large projected safety margin (50×) from the lowest dose tested in 6-month monkey study. The predicted receptor occupancy distribution for the 1.25 mg every other week is expected to fall below 80% for the entire treatment population, while this dose is expected to maintain receptor occupancy above 40% for majority of the human subjects. Based on the above findings of the correlation between 80% receptor occupancy and KLH suppression, the 5 mg every other week regimen is expected to elicit >80% receptor occupancy in approximately 50% of the patients, thereby providing some immunosuppressive activity, which is expected to induce some clinical response, albeit suboptimal. Furthermore the exposure (AUC(TAU)) associated with this dosing regimen are fairly low with a large projected safety margin (12.7×) from the lowest tested dose in 6-month monkey toxicology study. The higher doses of 12.5 mg every other week and every week are expected to provide >80% and >90% receptor occupancy for the entire treatment population, and expected to elicit near maximal immunosuppressive activity potentially leading to near maximal efficacious response. The exposures associated with these 2 regimens are considerably lower (5.1× and 2.5×), than that of the lowest tested dose in 6-month monkey study. The projected exposures of the four doses are within the range of exposures tested in the MAD study in healthy human subjects. The highest dose in this POC study will still be one third of the highest dose in the MAD study.

Example 6: Study Design and Duration

Figure 2:
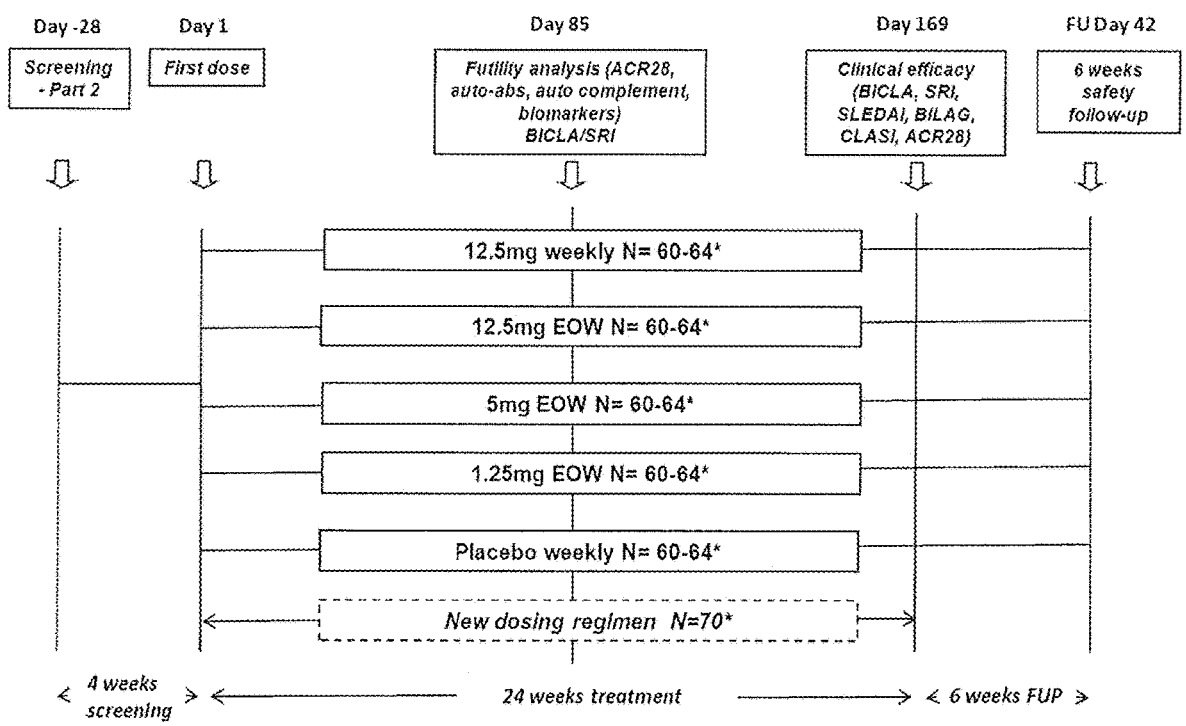
FIG. 2 shows Part 2 of an FDA Phase 2 parallel-arm, randomized, double-blinded, multicenter, international study, adaptive design schematic for BMS-931699.
Figure 3:
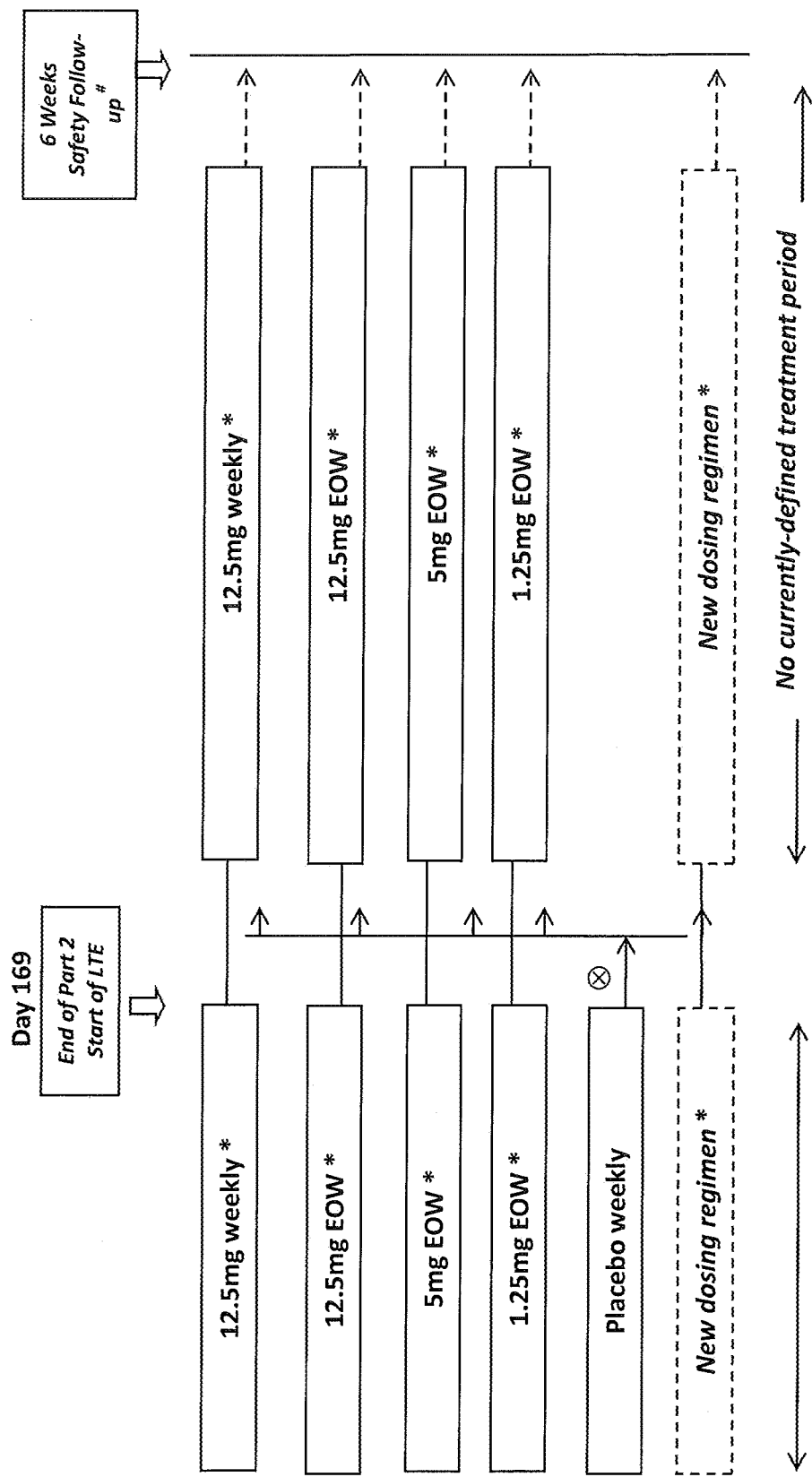
FIG. 3 shows the long term extension (LTE) design schematic.

A Phase 2, parallel-arm, randomized, double-blinded, multicenter, international study, with an adaptive design is conducted. The study comprises a short-term period which has two parts: Part 1 (FIG. 1) and Part 2 (FIG. 2), and a long-term extension (LTE) period (FIG. 3).

Part 1 focuses on assessing safety and receptor occupancy. Part 1 is limited to 30 to 50 patients (approximately 6-10 patients/arm) are included in the Safety/RO interim analysis (IA). The 6 to 10 patients per arm complete 28 days (4 weeks) of treatment. These patients continue study treatment beyond the IA for Safety/RO and be treated for up to 24 weeks and be followed for 6 additional weeks after treatment is completed. A total of up to 50 randomized subjects are treated for up to 6 months. Treatment could be shorter if IA for Safety/RO analysis indicates that one or more arms should be dropped.

Part 2 is opened once the cumulative safety profile is considered acceptable and receptor occupancy data for 6-10 subjects per cohort dosed for >28 days is available. Approximately 300 subjects are randomized into this part of the study (number of patient to be randomized into Part 2 may increase based on the results of the futility interim analysis). All subjects undergo screening evaluations to determine eligibility and allow down titration of prednisone (or prednisone equivalent) within 28 days prior to administration of their first dose of study medication. The dose may be adapted as follows:

Safety and receptor occupancy (RO) interim analysis: a safety and receptor occupancy analysis is performed when approximately 6 to 10 subjects per arm have reached Study Day 29 (4 weeks of treatment). Based on the results of the analysis, the arm dose may be adjusted or dropped completely.

Interim analysis for futility and dose adaption on BICLA response, SLE Responder Index response, ACR28 and some SLE biomarkers (such as auto-antibodies, complement levels, etc.) with possible exploratory exposure response analysis, is performed when approximately 30 subjects per arm have reached Study Day 85 (12 weeks of treatment or discontinued). Analysis is performed by an unblinded Sponsor team, while maintaining blind at the site and subject level. Based on the results, the dose levels and sample size may be modified.

Ongoing assessment of safety is performed by an independent Data Monitoring Committee (DMC) and an internal unblinded safety monitoring team. Both entities may make recommendations to the Sponsor regarding conduct of study and dose adjustment based on safety observations.

The long-term extension (LTE) period is optional and includes eligible subjects who have completed Day 169 (week 24) of treatment and consent to participate. This period of the study remains blinded but no longer has a placebo arm. Eligible subjects remain on their originally-assigned dose arm, unless they were on the placebo arm during the short-term period. Placebo-arm subjects are re-randomized into one of the existing active arms at Day 169 (24 weeks). Re-randomization of the placebo subjects is done by IVRS and only the unblinded pharmacist/drug preparer knows the new randomization arm. The LTE remains blinded to the study team and study personnel.

The approximate duration of the study is 28 days (4 weeks) of screening, 168 days (24 weeks) of treatment, and 42 days (6 weeks) of safety follow-up, for a total of approximately 238 days (34 weeks) in the short-term period. If the subject is eligible and opts to continue into the LTE, the 42 day follow-up visit is performed after the short-term period is completed and the subject enters LTE directly. If the subject opts not to enter LTE then a follow-up visit is completed 42 days after end of treatment. At the time of writing there is no defined end date to the long term extension period, however, the LTE provision may be further adjusted based on results from the ongoing lulizumab development program. Subjects discontinuing treatment during the LTE period complete the follow-up visit approximately 6 weeks after receiving their last dose of study medication.

Subjects randomized in either Part 1 or Part 2 are treated for up to 24 weeks and have the same procedures performed and follow the same visit schedule.

Example 7: Overall Risk/Benefit Assessment

This Example summarizes potential risks of treatment with BMS-931699 and the precautions that are required in clinical studies. This assessment is based on nonclinical data and the clinical experience to date with BMS-931699 set forth in the previous Examples.

Blocking the function of CD28 is expected to modulate the immune response. Modulation of immune response may predispose to infection. In nonclinical studies, there was no evidence that BMS-913699 treatment resulted in bacterial or viral infection. To date, single doses and repeat doses of BMS-931699 have been administered in healthy subjects. Based on results from both single- and repeat-dose IV and SC nonclinical toxicology studies in cynomolgus monkeys and the clinical data from studies IM128001 and IM128003, BMS-931699 has demonstrated an acceptable safety profile, supporting continued development.

The expected exposure [AUC(TAU)] at steady state for the highest proposed dose 12.5 mg weekly is approximately 2.5× lower than the lowest tested dose of 1 mg/kg/week in the 6 month toxicity study in monkeys where minimal to moderate vacuolation of macrophages were observed. The highest dose in this Phase 2 study is one third of the highest dose in the MAD study. Intense safety monitoring is put in place during Part 1 of Phase 2, allowing early detection of any safety signals.

Example 8: Dose Adaptation

As discussed above, the Phase 2 study initiates with the 4 regimens of 1.25 mg every other week, 5 mg every other week, 12.5 mg every other week, and 12.5 mg weekly. Safety/receptor occupancy interim analysis is performed to ensure the exposures and receptor occupancy observations approximate the original predictions.

An interim analysis (IA) for safety and receptor occupancy is performed in Part 1 of the study, when at least 6 patients per treatment arm have reached Study Day 29. That receptor occupancy observations approximate the original predictions and BMS-931699 is well tolerated in SLE patients is confirmed. The rest of the patients are enrolled in the study.

Based on the results of this interim analysis, dosing regimens originally included in Part 1 may be discontinued and/or new dosing regimens may be added according to the criteria outlined below. Enrollment in Part 2 of the study is opened after the IA has resulted in a decision regarding the dosing regimens to be carried forward:

Safety

The safety analysis focuses on incidence and severity of all adverse events (AEs), serious AEs and pre-established Events of Special Interest such as infection AEs and any other safety analysis requested by DMC. The DMC in conjunction with an unblinded internal safety monitoring team may require one or more doses to be discontinued if stopping criteria are met or other safety signals arise that the Medical Monitor and/or DMC consider of sufficient concern. The unblinded safety monitoring team is not involved in the regular study activities.

Receptor Occupancy

The median receptor occupancy at Day 29 for each treatment arm is calculated.

If median receptor occupancy of any dose is <20%, the sponsor considers dropping that dose.

If the median receptor occupancy for all doses is >90% the sponsor considers adding or replacing a dose in Part 2 of the study to ensure an adequate pharmacodynamic range (dose not to exceed 12.5 mg weekly).

Dose decrease and/or reduction of frequency of administration is considered if receptor occupancy results fall outside the parameters indicated above. This adjustment occurs for safety reasons or in case unforeseen receptor occupancy profiles are observed in SLE patients. The decision to adjust dose and/or frequency is taken after review of the data by the clinical team. Subjects do not change dose. If an arm is modified or removed, subjects randomized to that arm and discontinued.

In Part 2 of the study, an interim analysis for futility and dose adaption occurs after 30 patients per treatment arm (including patients from Part 1) have completed at least 85 days of treatment period or discontinued. One or more treatment arms may be dropped for lack of efficacy, or a treatment arm may be added to explore a suboptimal dose. Exposure-response analysis for efficacy and safety may be conducted in parallel with this interim analysis to facilitate the dose selection for this additional lower treatment arm.

The long-term extension period has interim analyses for dose adaptation. If a significant safety concern is identified, one or more dose arms may be dropped. If one or more dose arms are dropped for safety reasons, all subjects currently receiving that or those dose(s) are discontinued from receiving study medication.

Example 9: Inclusion Criteria

Men or women (not nursing or pregnant) between 18 and 70 years of age who meet the American College of Rheumatology criteria for the classification of Systemic Lupus Erythematosus are eligible (Table 3). The classification is based on 11 criteria. For the purpose of identifying patients in clinical studies, a person shall be said to have systemic lupus erythematosus (SLE) if any 4 or more of the 11 criteria are present, serially (sequentially) or simultaneously (coincident), during any interval of observation. Four criteria must be met prior to dosing on Day 1 for entry into the study. However, the 4 criteria need not be present at study entry, but have occurred at some time during the course of the disease and be documented:

TABLE 3

The 1982 Revised Criteria for Classification of Systemic Lupus Erythematosus

| Criterion | Definition |
|---|---|
| 1) Malar rash | Fixed erythema, flat or raised, over the malar eminences, tending to spare the nasolabial folds |
| 2) Discoid rash | Erythematous raised patches with adherent keratotic scaling and follicular plugging; atrophic scarring may occur in older lesions |
| 3) Photosensitivity | Skin rash as a result of unusual reaction to sunlight, by patient history or physician observation |
| 4) Oral ulcers | Oral or nasopharyngeal ulceration, usually painless, observed by physician |
| 5) Arthritis | Nonerosive arthritis involving 2 or more peripheral joints, characterized by tenderness, swelling, or effusion |
| 6) Serositis | a) Pleuritis--convincing history of pleuritic pain or rubbing heard by a physician or evidence of pleural effusion<br>OR<br>b) Pericarditis--documented by ECG or rub or evidence of pericardial effusion |
| 7) Renal disorder | a) Persistent proteinuria greater than 0.5 grams per day or greater than 3+ if quantitation not performed<br>OR<br>b) Cellular casts--may be red cell, hemoglobin, granular, tubular, or mixed |
| 8) Neurologic | a) Seizures--in the absence of offending drugs or known metabolic disorder derangements; e.g., uremia, ketoacidosis, or electrolyte imbalance<br>OR<br>b) Psychosis--in the absence of offending drugs or known metabolic derangements, e.g., uremia, ketoacidosis, or electrolyte imbalance |
| 9) Hematologic disorder | a) Hemolytic anemia--with reticulocytosis<br>OR<br>b) Leukopenia--less than 4,000/mm$^3$ total on 2 or more occasions<br>OR<br>c) Lymphopenia--less than 1,500/mm$^3$ on 2 or more occasions<br>OR<br>d) Thrombocytopenia--less than 100,000/mm$^3$ in the absence of offending drugs |
| 10) Immunologic disorder | a) Anti-DNA: antibody to native DNA in abnormal titer<br>OR<br>b) Anti-Sm: presence of antibody to Sm nuclear antigen<br>OR<br>c) Positive finding of anti-phospholipid antibodies based:<br>1) an abnormal serum level of IgG or IgM anti-cardiolipin antibodies,<br>2) a positive test result for lupus anticoagulant using a standard method,<br>or<br>3) a false positive serologic test for syphilis known to be positive for at least 6 months and confirmed by Treponema pallidum immobilization or fluorescent treponemal antibody absorption test. |
| 11) Antinuclear antibody | An abnormal titer of antinuclear antibody by immunofluorescence or an equivalent assay at any point in time and in the absence of drugs known to be associated with "drug-induced lupus" syndrome |

In addition:

Subjects have elevated anti-nuclear antibody at screening of ≥1:80 via immunofluorescent assay at the central laboratory and/or positive anti-dsDNA and/or anti-Sm above the normal level as determined by the central laboratory. (If central laboratory results are negative and positive results are documented at the site, a single repeat of the central laboratory values is allowed.)

Subjects also have a Systemic Lupus Erythematosus Disease Activity Index 2000 (SLEDAI-2K) score at screening of ≥6 to be eligible. At least 4 of the points are attributable to clinical criteria including at least one of the following clinical parameters: arthritis, rash, myositis, mucosal ulcers, pleurisy, pericarditis, vasculitis and excluding points from lupus headache and organic brain syndrome.

On Day 1, subjects have a SLEDAI-2K score of ≥4 including points from at least one of the following clinical components: arthritis, rash, myositis, mucosal ulcers, pleurisy, pericarditis, vasculitis, and fever and excluding parameters which require central laboratory results (hematuria, pyuria, urinary casts, proteinuria, positive anti-dsDNA, decreased complement, thrombocytopenia and leukopenia). Points from lupus headache and organic brain syndrome are excluded.

Subjects have at least one of the following manifestations of SLE, as defined by the British Isles Lupus Assessment Group (BILAG) 2004 criteria as modified for use in this study:

(1) BILAG A or B score in the Mucocutaneous body system
(2) BILAG A or B score in the Musculoskeletal body system due to active polyarthritis defined as follows:
   (a) "BILAG A": severe arthritis (BILAG #41) manifested by observed active synovitis in ≥2 joints with marked loss of functional range of movements and significant impairment of basic activities of daily living, that has been present on several days cumulatively over the past 4 weeks, including at the time of the screening visit. Basic ADLs are defined as the following activities which require assistance or assistive devices (at least one must be present and documented in source): ambulation, toileting, grooming including bathing, dressing, feeding oneself (not responsive to steroids up to 10 mg/day, antimalarials, NSAIDs).
- (b) "BILAG B": Moderate arthritis or tendonitis or tenosynovitis (BILAG #42) defined as tendonitis/tenosynovitis or active synovitis in ≥1 joint (observed or through history) with some loss of functional range of movements which lead to some loss of functional range of motion as manifested by effects on instrumental ADLs (such as cooking, driving, using the telephone or computer, shopping, cleaning, etc.) which has been present on several days over the last 4 weeks and is present at the time of the screening visit.
- (3) if only one "B" and no "A" score is present in the Mucocutaneous body system or in the Musculoskeletal body system due to arthritis, then at least one B must be present in the other body systems for a total of 2 "B" BILAG body system scores.

Unless intolerant, subjects must be currently receiving at least one of the following steroid-sparing agents for a minimum of 12 weeks, and a stable dose for at least 56 days (8 weeks) prior to signing consent: azathioprine (AZA), chloroquine, hydroxychloroquine, methotrexate (MTX), leflunomide, mycophenolate mofetil/mycophenolic acid. Subjects must remain on stable dose throughout the study.

Prednisone (or prednisone-equivalent) is not required; however, if subject is taking prednisone (or prednisone equivalent), the dose cannot exceed 30 mg/day at screening for a subject to be eligible and must be stable at a maximum of 10 mg/day for at least 5 days prior to Day 1 (randomization). Any other immunosuppressive or biologic drug requires washout periods prior to study entry. If subjects are receiving non-steroidal anti-inflammatory drugs (NSAIDs) (including marketed COX-2 inhibitors), doses must be stable for 14 days prior to first dose of study medication on Day 1 (randomization) and subject must remain on the same dose throughout the study. Note: NSAIDS should be withheld for at least 12 hours prior to visits where BILAG, SLEDAI 2K, joint counts, Cutaneous Lupus Erythematosus Disease Area and Severity Index (CLASI) and MDGA is assessed.

Female patients of childbearing potential have a negative serum or urine pregnancy test (minimum sensitivity 25 IU/L or equivalent units of human chorionic gonadotropin) within 24 hours prior to the start of study drug administration. Female patients are not breastfeeding. Female patients of childbearing potential must use contraception for the duration of treatment with study drug plus 5 half-lives of study drug (7 days) plus 30 days (duration of ovulatory cycle) for a total of 65 days post-treatment completion. Males who are sexually active with female patients of childbearing potential must use contraception for the duration of treatment with study drug plus 5 half-lives of the study drug (7 days) plus 90 days (duration of sperm turnover) for a total of 125 days post-treatment completion. Azoospermic males and women of child bearing potential who are continuously not heterosexually active are exempt from contraceptive requirements. However they must still undergo pregnancy testing.

Example 10: Exclusion Criteria

The following subjects are not enrolled in the Phase 2 study:
- a) Subjects with drug-induced SLE, rather than "idiopathic" SLE.
- b) Subjects with other autoimmune disease [(for example rheumatoid arthritis (RA), multiple sclerosis (MS)]. (Subjects with type 1 diabetes mellitus, thyroid autoimmune disease and secondary Sjögren syndrome are eligible.)
- c) Subjects with primary anti-phospholipid antibody syndrome as the sole or primary feature of their SLE or SLE-like syndrome are excluded. However, subjects with secondary anti-phospholipid syndrome are included in the study, unless they have had a serious thrombotic event (e.g. pulmonary embolism, stroke, or deep vein thrombosis) within one year prior to signing consent. Subjects on chronic coumadin or enoxaparin can be enrolled in the study.

Subjects with the following medical conditions, concomitant illnesses and medical histories are not enrolled in the Phase 2 study:
- a) Subjects with any major surgery within 6 weeks of study drug administration (Day 1) or any elective surgery planned during the course of the study.
- b) Subjects with any history or risk for tuberculosis (TB), specifically subjects with:
  - (1) Current clinical, radiographic or laboratory evidence of active TB.
  - (2) A history of active TB within the last 3 years, unless there is documentation that prior anti-TB treatment was appropriate in duration and type according to current World Health Organization Guidelines.
  - (3) Latent TB defined as Positive quantiferon (QFG) or other diagnostic test in the absence of clinical manifestations, unless subject has received at least 1 month treatment with Isoniazid, or other agents recommended by local Health Authority guidelines, and an interferon gamma release assay (IGRA) test, eg, QFG or T-Spot, is negative before Day 1.
  - (4) Positive QFG test (or other diagnostic test) at screening or within 3 months prior to Day 1 is acceptable as long as there is documentation of a negative result by Day 1.
- c) Subjects with active or unstable lupus neuropsychiatric manifestations, including but not limited to any condition defined by BILAG "A" criteria, with the exception of mononeritis multiplex and polyneuropathy which are allowed.
- d) Subjects with active, severe, lupus nephritis (WHO class III, IV) which requires or may require treatment with cytotoxic agents or high dose corticosteroids. Subjects with prior, controlled renal disease with residual proteinuria up to 3 g/day or a urine protein/creatinine ratio of 3 mg/mg or 339 mg/mmol are allowed.
- e) Subjects with herpes zoster that resolved less than 2 months prior to screening.
- f) Subjects with evidence (as assessed by the Investigator) of active or latent bacterial or viral infections at the time of potential screening, including subjects with evidence of Human Immunodeficiency Virus (HIV) infection as defined by positivity of HIV-1, -2 antibody.
- g) Subjects currently on hydroxychloroquine or chloroquine with evidence of retinopathy within 6 months of screening or who have had no ophthalmologic evaluation within one year of screening and do not have this examination done or who are unwilling or unable to have regular ophthalmologic examinations while participating in the study.
h) Concomitant illness that, in the opinion of the investigator, is likely to require additional systemic glucocorticosteroid therapy during the study, (e.g., asthma) is exclusionary. However, treatment for asthma with inhalational corticosteroid therapy is allowed.
i) Female subjects with a breast cancer screening suspicious for malignancy, and in whom the possibility of malignancy cannot be reasonably excluded following additional clinical, laboratory or other diagnostic evaluations.
j) Subjects with a history of cancer within the last five years (other than non-melanoma skin cell cancers cured by local resection). Existing non-melanoma skin cell cancers must be removed prior to randomization (Day 1 treatment). Carcinoma in situ, treated with definitive surgical intervention, is allowed.
k) Subjects with any acute and/or chronic serious bacterial or viral infection (such as pneumonia, renal infection and sinusitis). Documentation of resolution must be available in medical chart prior to Day 1 (randomization).
g) Donation of blood to a blood bank or in a clinical study (except a screening visit) within 4 weeks of study drug administration (within 2 weeks for plasma only).
h) Blood transfusion within 4 weeks of study drug administration.
i) Subjects with an inability to be venipunctured and/or tolerate venous access.
j) Subjects with a history of any significant drug allergy (such as anaphylaxis or hepatotoxicity).
k) Any other sound medical, psychiatric, and/or social reason as determined by the investigator.

Subjects with the following medical conditions, concomitant illnesses and medical histories are not enrolled in the Phase 2 study:
a) Evidence of organ dysfunction or any clinically significant deviation from normal in physical examination, vital signs, ECG or clinical laboratory determinations beyond what is consistent with the target population.
b) Positive hepatitis-B surface antigen.
c) Positive hepatitis-C antibody with positive Recombinant ImmunoBlot Assay (RIBA) or Polymerase Chain Reaction (PCR).
d) White blood cells (WBC)<1,200/mm3 (1.2×109/L).
e) Platelets <50,000/mm3 (50×109/L).
f) Hemoglobin <8 g/dL or <7 g/dL if due to hemolytic anemia related to SLE.
g) Proteinuria >3.0 g/day (3000 mg/day) or equivalent level of proteinuria as assessed by protein/creatinine ratio (3 mg/mg or 339 mg/mmol).
h) Serum creatinine >2.0 mg/dL.
i) Active urinary sediment defined as red blood cell (RBC) casts.
j) Serum alanine aminotransferase (ALT) >2× upper limit of normal (ULN), unless explicitly related to lupus based on the Investigator's judgment.
k) Serum aspartate aminotransferase (AST) >2×ULN, unless explicitly related to lupus based on the Investigator's judgment.
l) Positive urine screen for illegal drugs of abuse, except if these drugs are prescribed by the treating physician (must be documented), and except for other drugs that are not illegal within the country or the region m) Any other laboratory test results that, in the opinion of the Investigator, might place subject at unacceptable risk for participating in this study.

Prohibited and/or restricted medications taken prior to study drug administration in the study are described below:
1) Prior exposure to BMS-931699.
2) Use of any other drugs, including over-the-counter medications and herbal preparations, within 1 week prior to study drug administration except those medications cleared by the BMS medical monitor.
3) The use of cyclophosphamide, any intravenous, any intra-articular or biologic agent is prohibited during the study.
4) For subjects who develop neutropenia (absolute neutrophil count <1.3×103/μL), dosing with mycophenolate mofetil/mycophenolic acid should be interrupted or dose reduces as per the package insert.
5) Subjects who have received any live vaccines within 30 days of screening. (Furthermore, live vaccines should not be used within the 2 months following last dose and any other inactivated vaccines such as tetanus etc. should be used according to local guidelines if at all during treatment period.)
6) Subjects who are scheduled or anticipated to have elective surgery during the course of the study.

No concomitant medications (prescription, over-the-counter or herbal) are to be administered during study unless they are prescribed by the investigator for treatment of specific clinical events.

Example 11: Administration of BMS-931699 or Placebo

BMS-931699 or a look alike placebo is administered weekly as a solution subcutaneously (SC) single injection, dependent on the dosage panel. The clinical label reflects the product name as "BMS-931699-01" to be linked with the product description on the vial. The composition of the BMS-931699-01 injection is 12.5 mg/mL BMS-931699 in 20 mM phosphate, pH 5.9, with 5% (w/v) sorbitol. The BMS-931699-01 injection is packaged in a 3 cc vial with a 13 mm opening, 1-panel, open label. The BMS-931699-1 injection appears clear to slightly opalescent, colorless to pale yellow solution. The BMS-931699-01 injection is stored refrigerated 2-8° C. (36-46° F.).

Table 4 below indicates the total dose and number of vials per dose for each dosage panel.

TABLE 4

Treatment Administration

| Treatment | Total Daily Dose | Formulation Strength | Number of Vials |
| --- | --- | --- | --- |
| 1 | 1.25 mg SC EOW | 12.5 mg/mL | 1 |
| 2 | 5 mg SC EOW | 12.5 mg/mL | 1 |
| 3 | 12.5 mg SC EOW | 12.5 mg/mL | 1 |
| 4 | 12.5 mg SC Weekly | 12.5 mg/mL | 1 |
| 5 | Placebo | Placebo | Normal Saline Solution (NSS) |

For subcutaneous (SC) dosing, no dilution of the drug product solution (12.5 mg/mL) is required for doses of 12.5 mg. However, doses of 5 mg and 1.25 mg require dilution. A 21-gauge, 1.5 inch (3.8 cm) sterile needle is used for withdrawal of this product from the vial, and a 27 gauge, 0.5 inch (1.3 cm) sterile needle is used for SC dosing. A conventional, commercially available polycarbonate syringe of appropriate size is used for withdrawal and administration. After withdrawal into an appropriate sized syringe, the product is administered within 4 hours. If not dosed immediately, filled syringes are kept at 2°-8° C. (36°-46° F.) with protection from light prior to use. The placebo for BMS-931699 injection is a normal saline solution, which is administered in a similar fashion as described for the BMS-931699 injection. Study personnel administer the dose to the subject.

On Day 1, subjects are randomized to one of the dosing arms in Table 4 in a 1:1:1:1:1 randomization scheme. In the morning on Day 1, each subject receives a single SC dose of either BMS-931699 or placebo. The primary point of injection is one of the upper arms. However other points of injections are acceptable. There are no restrictions related to food and fluid intake associated with BMS-931699 known at this point.

Every randomized subject is required to come to the clinic/research center weekly to be dosed. This ensures double-blind is maintained despite the variability of regimens. Subjects randomized to weekly subcutaneous injections of either placebo or BMS-931699 are dosed weekly as per schedule and subjects randomized to one of the every other week arm are alternating between receiving a subcutaneous injection of BMS-931699 one week and one of placebo the following week.

Example 12: Biomarkers

Pharmacodynamic, target engagement and disease related biomarker assays are incorporated into the study inform dose selection, monitor efficacy and potentially predict treatment response. Blood and urine are drawn for the measurement of markers of target engagement and pharmacodynamic effects of BMS-931699 including CD28 receptor occupancy, C3, C4, and auto-antibodies.

Target engagement, as assessed by CD28 receptor occupancy on T cells, is incorporated into the study to inform dose selection for the Phase 3 study, monitor efficacy and potentially predict treatment response. The relationship between the concentration levels of BMS-931699 and the CD28 receptor occupancy is characterized.

Other biomarkers include: other cytokines and chemokines, anti-double-stranded deoxyribonucleic acid (anti-dsDNA), anti-nuclear antibody (anti-ANA), anti-Ro (otherwise known as anti-SSA, anti-SSA/RO, or anti-Ro/SSA) autoantibodies, anti-Lupus (anti-La)(otherwise known as anti-Sjögren syndrome type B antigen (anti-SS-B)) autoantibodies, anti-ribonuclear protein (anti-RNP) autoantibodies, anti-Sm nuclear antigen autoantibodies, anti-APL autoantibodies, and other autoantibodies. C-reactive protein (CRP), total immunoglobulin G (IgG), total immunoglobulin M (IgM), RNA transcripts in whole blood, proteins in urine (NGAL, TWEAK, MCP-1, IL-18, IL-1), total soluble CD28, T cell activation, leukocyte phenotypes in peripheral blood mononuclear cells (PMBCs) and whole blood (surface CD4, surface CD8, surface CD28, surface CD57 and intracellular granzyme B), soluble inflammatory mediators (serum TL-6, IL-18, TNF-α, α-interferon, BLyS(BAFF), CD154, sCD28 and other soluble receptors, microvessicles) can also serve as biomarkers.

Some pharmacodynamic endpoints relevant to SLE are characterized below:

Blood-Based (RNA) Assessments

The whole blood ribonucleic acid (RNA) sample is collected in PAX gene tubes at times indicated. These samples provide broad genomic profiling to search for novel pharmacodynamic and efficacy biomarkers related to inflammatory and/or autoimmune pathways. Furthermore, these samples are used to search for gene expressions at baseline that may be predictive of efficacy for BMS-931699 treated subjects.

Leukocyte Phenotyping

Peripheral blood is collected for immunophenotyping by flow cytometry. T cells may be characterized for activation and for subpopulations. Markers may include combinations of, but not limited to, surface CD4, CD8, CD28, CD57, and intracellular granzyme B. Other peripheral cells, including B cells, monocytes/macrophages, dendritic cells, and NK cells may be analyzed.

Urine Biomarkers

Urine is collected and analyzed for markers of SLE and other inflammatory disorders. The samples are analyzed for proteomic profiles of inflammatory markers (including but not limited to IL-18, IL-1, NGAL, uTWEAK, MCP-1). Exploratory analysis is carried out to identify biomarkers to monitor PD and response to therapy in patients with kidney involvement.

Peripheral Blood Serum and Plasma Biomarkers

Serum and plasma is collected for the measurement of soluble inflammatory mediators associated with inflammation, SLE or co-stimulation blockade (including, but not limited to, serum TL-6, IL-18, TNF-α, α-interferon, BLyS (BAFF), CD154, sCD28 and other soluble receptors, microvessicles). Exploratory analysis is carried out to identify biomarkers of SLE, and to monitor PD and the impact of BMS-931699 on inflammatory pathways.

Outcomes Research Assessments

Subjects complete the Functional Assessment of Chronic Illness Therapy-Fatigue (FACIT-F), the FDA Short Form-36 Questionnaire (SF-36) and the Subject's Global Assessment of Disease Activity (PGA). These pages are source documents in this study. All outcome research assessments should be completed prior to study drug administration at scheduled office visits.

Exploratory Efficacy Outcome Measures

Health-Related Quality of Life

The SF-36 is used to measure health-related quality of life. Individual subscale scores and two summary scores are calculated: (1) physical component summary (PCS) which includes physical functioning, role-physical, bodily pain, and general health; (2) mental component summary (MCS) which includes vitality, social functioning, roleemotional, and mental health. The SF-36 is a widely recognized tool that is recognized by the FDA as a validated instrument to measure health-related quality of life across multiple disease states.

Fatigue

Fatigue is assessed by the FACIT-F. FACIT-F is a health related quality of life questionnaire focused on Fatigue. FACIT-F includes the following components; physical well-being, social/family well-being, emotional well-being, functional well-being and additional concerns.

The disclosure set forth herein has been particularly shown and described with references to specific embodiments thereof. It will be understood by those skilled in the art that various changes in form and details may be made therein without departing from the scope encompassed by the appended claims.

What is claimed is:

1. A method of treating systemic lupus erythematosus (SLE) in a patient, comprising administering to the patient a therapeutically effective amount of an anti-CD28 domain antibody which comprises a variable domain, wherein the variable domain comprises the amino acid sequence of SEQ ID NO: 12 (1h-239-891(D70C)), wherein the anti-CD28 domain antibody is administered subcutaneously at a dose selected from about 1.25 mg, about 5 mg, and about 12.5 mg every week or every two weeks.

2. The method of claim 1, wherein the variable domain of the anti-CD28 domain antibody comprises: (1) a CDR1 region having the amino acid sequence of SEQ ID NO: 1; (2) a CDR2 region having the amino acid sequence of SEQ ID NO: 2; and (3) a CDR3 region having the amino acid sequence of SEQ ID NO: 3.

3. The method of claim 1, wherein the anti-CD28 domain antibody further comprises a 40 kDa branched polyethylene glycol.

4. The method of claim 1, wherein the dose is about 1.25 mg.

5. The method of claim 1, wherein the dose is about 5 mg.

6. The method of claim 1, wherein the dose is about 12.5 mg.

7. The method of claim 1, wherein the dose is administered every week.

8. The method of claim 1, wherein the dose is administered every two weeks.

9. The method of claim 1, wherein at least 2 doses are administered.

10. The method of claim 9, wherein the at least 2 doses are the same or different.

11. The method of claim 1, wherein at least 12 doses are administered.

12. The method of claim 1, wherein at least 24 doses are administered.

13. The method of claim 1, further comprising administering to the patient an immunosuppressive agent or an anti-inflammatory agent.

14. The method of claim 13, wherein the immunosuppressive agent or the anti-inflammatory agent is administered before or after the anti-CD28 domain antibody.

15. The method of claim 13, wherein the immunosuppressive agent or the anti-inflammatory agent is administered concurrently with the anti-CD28 domain antibody.

* * * * *

SEQUENCE LISTING

<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Arg Ala Ser Arg Pro Ile Trp Pro Phe Leu Glu
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Phe Thr Ser Arg Leu Arg His
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Leu Gln Asn Val Ala Asn Pro Ala Thr
1               5

<210> SEQ ID NO 4
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 5
<211> LENGTH: 108
<212> TYPE: PRT
<213> ORGANISM: Artificial Sequence
<220> FEATURE:
<223> OTHER INFORMATION: Synthetic Peptide -continued

<400> SEQUENCE: 5

Asp Ile Cys Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 6
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 6

Asp Ile Gln Met Thr Gln Ser Pro Cys Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 7
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 7

Asp Ile Gln Met Thr Gln Ser Pro Ser Ser Leu Ser Ala Ser Val Gly
1               5                   10                  15

Asp Cys Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 8
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Cys Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Cys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Cys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 11
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Cys Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 12
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Cys Phe Thr Leu Thr Ile Ser Ser Leu Gln Pro
65                  70                  75                  80

Glu Asp Phe Ala Thr Tyr Tyr Cys Leu Gln Asn Val Ala Asn Pro Ala
                85                  90                  95

```
Thr Phe Ser Gln Gly Thr Lys Val Glu Ile Lys Arg
            100                 105

<210> SEQ ID NO 13
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Cys Ile Ser Ser Leu Gln Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 14
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Trp Pro Phe
            20                  25                  30

Leu Glu Trp Tyr Gln Gln Lys Pro Gly Lys Ala Pro Lys Leu Leu Ile
        35                  40                  45

Tyr Phe Thr Ser Arg Leu Arg His Gly Val Pro Ser Arg Phe Ser Gly
    50                  55                  60

Ser Gly Ser Gly Thr Asp Phe Thr Leu Thr Ile Ser Ser Leu Cys Pro
65                  70                  75                  80

Glu Asp Phe Ala Thr Tyr Tyr Cys Leu Gln Asn Val Ala Asn Pro Ala
                85                  90                  95

Thr Phe Ser Gln Gly Thr Lys Val Glu Ile Lys Arg
            100                 105

<210> SEQ ID NO 15
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 15

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Arg Pro Ile Trp Pro Phe
            20              25              30

Leu Glu Trp Tyr Gln Gln Lys Pro Gly Lys Ala Pro Lys Leu Leu Ile
        35              40              45

Tyr Phe Thr Ser Arg Leu Arg His Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Leu Gln Asn Val Ala Asn Pro Ala
            85              90              95

Thr Phe Ser Gln Gly Thr Cys Val Glu Ile Lys Arg
            100             105
```